United States Patent
Kramer et al.

(10) Patent No.: US 9,504,833 B2
(45) Date of Patent: *Nov. 29, 2016

(54) AUTONOMIC MODULATION USING TRANSIENT RESPONSE WITH INTERMITTENT NEURAL STIMULATION

(71) Applicant: Cardiac Pacemakers, Inc., St. Paul, MN (US)

(72) Inventors: Andrew P. Kramer, Marine on St. Croix, MN (US); Jason J. Hamann, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/842,154

(22) Filed: Sep. 1, 2015

(65) Prior Publication Data

US 2015/0367134 A1 Dec. 24, 2015

Related U.S. Application Data

(63) Continuation of application No. 13/086,806, filed on Apr. 14, 2011, now Pat. No. 9,126,044.

(60) Provisional application No. 61/324,532, filed on Apr. 15, 2010.

(51) Int. Cl.
*A61N 1/36* (2006.01)
*A61N 1/05* (2006.01)

(52) U.S. Cl.
CPC ....... *A61N 1/36139* (2013.01); *A61N 1/36053* (2013.01); *A61N 1/36114* (2013.01); *A61N 1/0551* (2013.01); *A61N 1/36117* (2013.01)

(58) Field of Classification Search
None
See application file for complete search history.

(56) References Cited

U.S. PATENT DOCUMENTS

| 4,305,402 A | 12/1981 | Katims |
| 7,123,961 B1 | 10/2006 | Kroll et al. |

(Continued)

FOREIGN PATENT DOCUMENTS

| AU | 2011239668 B2 | 4/2014 |
| JP | 2005-532872 A | 11/2005 |

(Continued)

OTHER PUBLICATIONS

"U.S. Appl. No. 13/086, Response filed Apr. 2, 2015 to Non Final Office Action mailed Oct. 3, 2014", 10 pgs.

(Continued)

*Primary Examiner* — Brian T Gedeon
*Assistant Examiner* — Ankit D Tejani
(74) *Attorney, Agent, or Firm* — Schwegman Lundberg & Woessner, P.A.

(57) ABSTRACT

In various method embodiments for operating an implantable neural stimulator to deliver a neural stimulation therapy to an autonomic neural target, the method comprises using the implantable neural stimulator to deliver the neural stimulation therapy to the autonomic neural target, and evaluating an evoked response to the neural stimulation bursts. The neural stimulation therapy includes a plurality of neural stimulation bursts where each neural stimulation burst includes a plurality of neural stimulation pulses and successive neural stimulation bursts are separated by a time without neural stimulation pulses. Evaluating the evoked response includes sensing the evoked response to the neural stimulation bursts where sensing the evoked response includes sensing at least one physiological parameter affected by the neural stimulation bursts, comparing the sensed evoked response against a baseline, and determining if the evoked response substantially returns to the baseline between neural stimulation bursts.

20 Claims, 21 Drawing Sheets

(56) References Cited

U.S. PATENT DOCUMENTS

| | | |
|---|---|---|
| 7,269,459 B1 | 9/2007 | Koh |
| 7,418,292 B2 | 8/2008 | Shafer |
| 7,486,991 B2 | 2/2009 | Libbus et al. |
| 7,561,923 B2 | 7/2009 | Libbus et al. |
| 7,647,114 B2 | 1/2010 | Libbus |
| 7,769,441 B2 | 8/2010 | Foreman et al. |
| 7,769,446 B2 | 8/2010 | Moffitt et al. |
| 7,769,450 B2 | 8/2010 | Libbus et al. |
| 7,783,349 B2 | 8/2010 | Libbus et al. |
| 7,783,353 B2 | 8/2010 | Libbus et al. |
| 7,801,601 B2 | 9/2010 | Maschino et al. |
| 7,801,603 B2 | 9/2010 | Westlund et al. |
| 7,801,604 B2 | 9/2010 | Brockway et al. |
| 7,869,881 B2 | 1/2011 | Libbus et al. |
| 7,873,413 B2 | 1/2011 | McCabe et al. |
| 7,894,895 B2 | 2/2011 | Libbus et al. |
| 7,962,216 B2 | 6/2011 | Sunagawa et al. |
| 9,126,044 B2 | 9/2015 | Kramer et al. |
| 2002/0183647 A1 | 12/2002 | Gozani et al. |
| 2005/0149132 A1 | 7/2005 | Libbus |
| 2006/0106429 A1 | 5/2006 | Libbus et al. |
| 2006/0135998 A1 | 6/2006 | Libbus et al. |
| 2006/0167497 A1 | 7/2006 | Armstrong et al. |
| 2006/0173494 A1 | 8/2006 | Armstrong et al. |
| 2006/0173495 A1 | 8/2006 | Armstrong et al. |
| 2007/0142874 A1 | 6/2007 | John |
| 2007/0244407 A1 | 10/2007 | Osorio |
| 2008/0015659 A1 | 1/2008 | Zhang et al. |
| 2008/0021504 A1 | 1/2008 | McCabe et al. |
| 2008/0046052 A1 | 2/2008 | Werder et al. |
| 2008/0058874 A1 | 3/2008 | Westlund et al. |
| 2008/0058892 A1 | 3/2008 | Haefner et al. |
| 2008/0228238 A1 | 9/2008 | Libbus |
| 2008/0234780 A1 | 9/2008 | Smith et al. |
| 2008/0319513 A1 | 12/2008 | Pu et al. |
| 2009/0125076 A1 | 5/2009 | Shuros et al. |
| 2009/0143838 A1 | 6/2009 | Libbus et al. |
| 2009/0248119 A1 | 10/2009 | Libbus et al. |
| 2009/0312810 A1 | 12/2009 | Yonce et al. |
| 2010/0042176 A1 | 2/2010 | Snell |
| 2010/0106226 A1 | 4/2010 | Libbus |
| 2010/0286740 A1 | 11/2010 | Libbus et al. |
| 2010/0286741 A1 | 11/2010 | Libbus et al. |
| 2010/0305634 A1 | 12/2010 | Moffitt et al. |
| 2011/0009914 A1 | 1/2011 | Brockway et al. |
| 2011/0257708 A1 | 10/2011 | Kramer et al. |

FOREIGN PATENT DOCUMENTS

| | | |
|---|---|---|
| JP | 4189448 B2 | 12/2008 |
| JP | 2009-531156 A | 9/2009 |
| JP | 2013-523410 A | 6/2013 |
| JP | 5624672 B2 | 10/2014 |
| WO | WO-2008/024557 A1 | 2/2008 |
| WO | WO-2009/129486 A2 | 10/2009 |
| WO | WO-2010/005482 A1 | 1/2010 |
| WO | WO-2010/019444 A1 | 2/2010 |
| WO | WO-2011/130488 A2 | 10/2011 |
| WO | WO-2011/130488 A3 | 10/2011 |

OTHER PUBLICATIONS

"U.S. Appl. No. 13/086,806, Response filed Jul. 11, 2013 to Non Final Office Action mailed Apr. 11, 2013", 17 pgs.

"U.S. Appl. No. 13/086,806, Advisory Action mailed Nov. 14, 2013", 3 pgs.

"U.S. Appl. No. 13/086,806, Final Office Action mailed Sep. 9, 2013", 16 pgs.

"U.S. Appl. No. 13/086,806, Non Final Office Action mailed Apr. 11, 2013", 14 pgs.

"U.S. Appl. No. 13/086,806, Non Final Office Action mailed Oct. 3, 2014", 15 pgs.

"U.S. Appl. No. 13/086,806, Notice of Allowance mailed May 1, 2015", 12 pgs.

"U.S. Appl. No. 13/086,806, Response filed Nov. 6, 2013 to Final Office Action mailed Sep. 9, 2013", 18 pgs.

"U.S. Appl. No. 13/086,806, Restriction Requirement mailed Feb. 4, 2013", 6 pgs.

"U.S. Appl. no. 13/086,806, Response filed Mar. 6, 2013 to Restriction Requirement mailed Feb. 4, 2013", 9 pgs.

Hincapie, et al., "Selective control of physiological response by temporally-patterned electrical stimulation of the canine vagus nerve", 33rd Annual International Conference of the IEEE EMBS, (Sep. 11, 2011), 3107-3110.

Australian Application Serial No. 2011239668, First Examination Report mailed Mar. 18, 2013, 5 pgs.

Australian Application Serial No. 2011239668, Subsequent Examiners Report mailed Sep. 6, 2013, 3 pgs.

International Application Serial No. PCT/US2011/032450, International Preliminary Report on Patentability mailed Oct. 26, 2012, 14 pgs.

International Application Serial No. PCT/US2011/032450, International Search Report mailed Feb. 20, 2012, 6 pgs.

International Application Serial No. PCT/US2011/032450, Partial Search Report mailed Dec. 9, 2011, 8 pgs.

International Application Serial No. PCT/US2011/032450, Written Opinion mailed Feb. 20, 2012, 13 pgs.

Japanese Application Serial No. 2013-505131, Office Action mailed Nov. 20, 2013, With Translation, 6 pgs.

Japanese Application Serial No. 2013-505131, Response filed Mar. 20, 2014 to Office Action mailed Nov. 20, 2013, W/ English Translation Of Claims, 12 pgs.

AUTONOMIC MODULATION USING TRANSIENT RESPONSE WITH INTERMITTENT NEURAL STIMULATION

CLAIM OF PRIORITY

This application is a continuation of U.S. application Ser. No. 13/086,806, filed Apr. 14, 2011, now issued as U.S. Pat. No. 9,126,044, which claims the benefit of priority under 35 U.S.C. §119(e) of U.S. Provisional Patent Application Ser. No. 61/324,532, filed on Apr. 15, 2010, each of which is herein incorporated by reference in its entirety.

TECHNICAL FIELD

This application relates generally to medical devices and, more particularly, to systems, devices and methods for delivering neural stimulation to modulate autonomic activity.

BACKGROUND

Neural stimulation has been proposed as a therapy for a number of conditions. Examples of neural stimulation therapies include neural stimulation therapies for respiratory problems such as sleep disordered breathing, blood pressure control such as to treat hypertension, cardiac rhythm management, myocardial infarction and ischemia, heart failure, epilepsy, depression, pain, migraines, eating disorders, obesity, inflammatory diseases, and movement disorders. Some current and proposed neural stimulation therapies are chronic therapies delivered for periods on the order of minutes, days, weeks, months and years. If the neural stimulation therapy is associated with an undesired response, the undesirability of the response may be exacerbated because of the chronic nature of the therapy. For example, the undesired response may have long-term consequences for the health or quality of life for the patient. It is thus desirable to reduce, minimize or eliminate undesired responses to neural stimulation therapies.

SUMMARY

In various method embodiments for operating an implantable neural stimulator to deliver a neural stimulation therapy to an autonomic neural target, the method comprises using the implantable neural stimulator to deliver the neural stimulation therapy to the autonomic neural target, and evaluating an evoked response to the neural stimulation bursts. The neural stimulation therapy includes a plurality of neural stimulation bursts where each neural stimulation burst includes a plurality of neural stimulation pulses and successive neural stimulation bursts are separated by a time without neural stimulation pulses. Evaluating the evoked response includes sensing the evoked response to the neural stimulation bursts where sensing the evoked response includes sensing at least one physiological parameter affected by the neural stimulation bursts, comparing the sensed evoked response against a baseline, and determining if the evoked response substantially returns to the baseline between neural stimulation bursts.

Various device embodiments for delivering a neural stimulation therapy to an autonomic neural target of a patient comprise a neural stimulator, a memory, a controller, a sensor, and a response extractor. The neural stimulator is configured to generate stimulation energy to stimulate the autonomic neural target. The memory has a programmed neural stimulation therapy stored therein. The therapy includes a plurality of programmable neural stimulation parameters for use in controlling a dose of the neural stimulation therapy. The neural stimulation therapy includes a plurality of neural stimulation bursts, each burst includes a plurality of neural stimulation pulses, and successive bursts are separated by a time without neural stimulation pulses. The controller is configured to communicate with the memory and the neural stimulator to control the neural stimulation therapy using the programmable parameters. The sensor is adapted to sense at least one physiological parameter indicative of an evoked response to the neural stimulation therapy. The response extractor is configured to receive a time series of parameter data from the sensor and to extract evoked response data from the time series of parameter data and configured to determine if the evoked response data substantially returns to the baseline between neural stimulation bursts.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
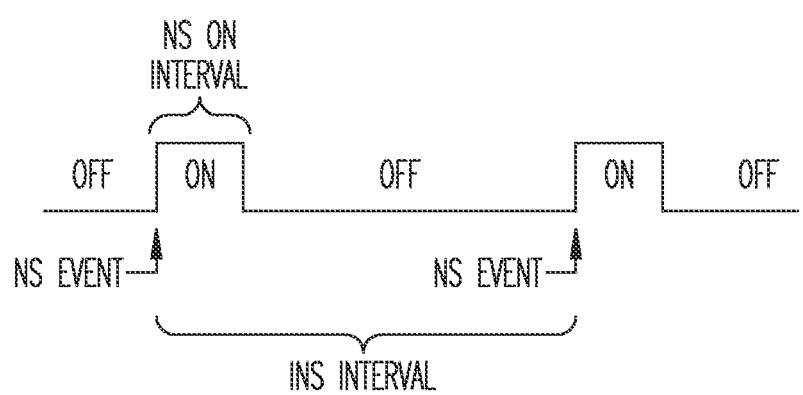
FIG. 1. illustrates a representation of intermittent neural stimulation (INS).

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter refers to intermittent neural stimulation (INS) of the autonomic nervous system (ANS), and further refers to systems and methods to control transient ANS responses caused directly and reflexively by the INS. Various embodiments of the present subject matter provide intermittent neural stimulation as a pattern of on and off periods of stimulation that evokes direct and reflex responses during the on period that diminish to baseline (i.e., wash out) during the off period. Responses that wash out between INS periods are called transient responses. A direct response is the immediate effect of ANS targets directly stimulated by the INS. A reflex response is a secondary effect of ANS reflex circuits stimulated by the direct response. Collectively, the transient direct and reflex ANS responses caused by the INS shall be referred to as the evoked response. The evoked response may have therapeutic and undesirable effects. The combination of direct and reflex ANS responses may be therapeutic. It is currently believed that it is desirable to control these direct and reflex responses to provide a transient balanced effect. By way of example and not limitation, it is believed that it is desirable for reflex responses to return to a baseline between stimulation bursts of an autonomic INS therapy. Additionally, for certain therapies, some direct physiological effects of neural stimulation such as heart rate and blood pressure changes may be undesirable, and it is believed to be desirable to control these undesired effects to be transient so that they return to baseline between stimulations. The present subject matter provides a means to monitor or measure ANS responses for an autonomic modulation therapy delivered with intermittent neural stimulation pulses, as a way of promoting transient balanced effects of the ANS and/or as a way of promoting the avoidance of undesirable physiological effects of the ANS. For example, the present subject matter can detect the transient evoked response and the return of the evoked response to a baseline before delivering a subsequent stimulation burst. The stimulation of the ANS can be controlled to allow the direct and reflex effects of neural stimulation to substantially return to baseline between stimulation periods.

FIG. 1. illustrates a representation of intermittent neural stimulation (INS). The figure diagrammatically shows the time-course of a neural stimulation that alternates between intervals of stimulation being ON, when one stimulation pulse or a set of grouped stimulation pulses (i.e., a burst) is delivered, and intervals of stimulation being OFF, when no stimulation pulses are delivered. The duration of the stimulation ON interval is sometimes referred to as the stimulation duration or burst duration. The start of a stimulation ON interval is a temporal reference point NS Event. The time interval between successive NS Events is the INS Interval, which is sometimes referred to as the stimulation period or burst period. For an application of neural stimulation to be intermittent, the stimulation duration (i.e., ON interval) must be less than the stimulation period (i.e., INS Interval) when the neural stimulation is being applied. The duration of the OFF intervals of INS are controlled by the durations of the ON interval and the INS Interval. The duration of the ON interval relative to the INS Interval (e.g., expressed as a ratio) is sometimes referred to as the duty cycle of the INS.

To assist the reader, a brief discussion of ANS physiology and the direct/reflex response to ANS modulation by INS is provided below, followed by a discussion of monitoring ANS response(s) to intermittent ANS stimulation and a discussion of various device and system embodiments.

ANS Physiology

The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

The heart rate and force is increased when the sympathetic nervous system is stimulated (the parasympathetic system in inhibited), and is decreased when the sympathetic nervous system is inhibited (the parasympathetic nervous system is stimulated). An afferent nerve conveys impulses toward a nerve center. An efferent nerve conveys impulses away from a nerve center.

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, increases digestion in the small intestine, increases urine secretion, and contracts the wall and relaxes the sphincter of the bladder. The functions associated with the sympathetic and parasympathetic nervous systems are many and can be complexly integrated with each other.

As identified above the sympathetic and parasympathetic systems provide opposite effects. The ANS reflexes tend to compensate for these effects, returning the physiologic system to an autonomic balance. For example, an event that causes an increase in sympathetic activity and/or decrease in parasympathetic activity causes an increase in sympathetic tone, which tends to cause the ANS reflexes to increase parasympathetic activity and/or decrease sympathetic activity to decrease the sympathetic tone after the event ends. Similarly, an event that causes a decrease in sympathetic activity and/or increase in parasympathetic activity causes an increase in parasympathetic tone, which tends to cause the ANS reflexes to decrease parasympathetic activity and/or increase sympathetic activity to decrease the parasympathetic tone after the event ends.

Direct Responses and Reflex Responses to ANS Modulation

Figure 2A:
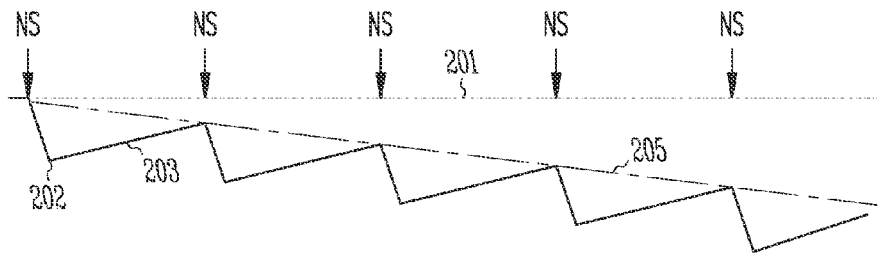
FIGS. 2A-2D illustrate representations of direct and reflex responses to neural stimulation of a physiological signal modulated by the ANS.
Figure 2B:
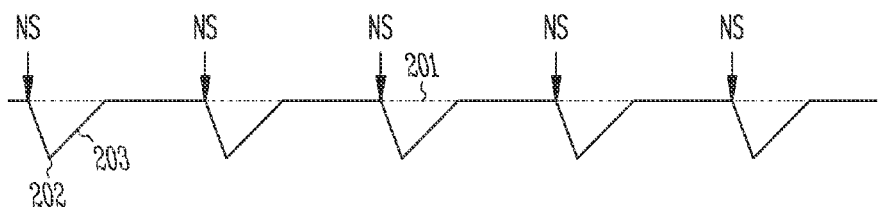
Figure 2C:
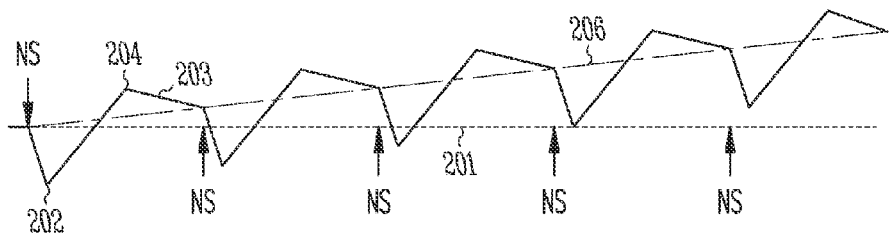
Figure 2D:
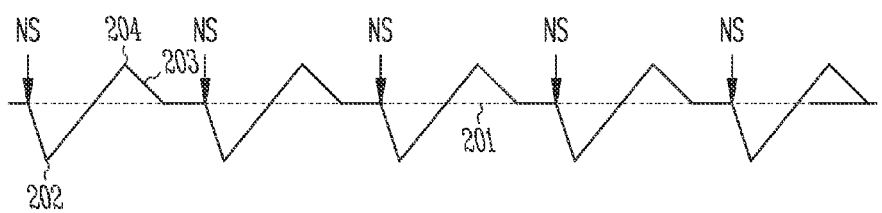

FIGS. 2A-2D illustrate representations of direct and reflex responses to neural stimulation of a physiological signal modulated by the ANS, e.g., heart rate. Such direct and reflex responses of the physiological signal typically are opposite, because the ANS functions to maintain a balance of opposing parasympathetic and sympathetic physiological effects. Direct parasympathetic responses and sympathetic reflex responses are illustrated within this document as an example. The present subject matter is also applicable to direct sympathetic responses and parasympathetic reflex responses. The portion of the signal below the initial baseline 201 represents the direct response 202 to neural stimulation pulses (NS pulse) that elicit a parasympathetic response, and the portion of the signal above the straight line 201 represents the sympathetic reflex response 204 after the direct response 202 ends. Various stimulation parameters can be selected to provide the desired direct and reflex response. FIG. 2A illustrates a period of INS when five neural stimulation ON periods (NS) are delivered where each NS evokes a direct response 202 only, which does not return to the initial baseline 201 between successive NS. This illustrates a direct response that is not transient during the INS. At each NS, the direct response 202 peaks below the initial baseline 201 followed by a recovery 203 back toward baseline 201. However this recovery does not return to baseline 201 before the next NS. As a result of the incomplete direct response recovery between successive NS, the subsequent signal baseline 205 progressively shifts lower below the initial baseline 201 after each NS of the INS. It is believed the effect of non-transient direct responses accumulating over repeated stimulations during INS may be undesirable in many clinical applications of neural stimulation. FIG. 2B illustrates a period of INS similar to FIG. 2A, except the stimulation parameters have been adjusted to cause the direct response 202 to return to the initial baseline 201 between successive NS. This illustrates a direct response that is transient during the INS. FIG. 2C illustrates a period of INS where each NS evokes a direct response 202 and a reflex response 204, which does not return to the initial baseline 201 between successive NS. This illustrates a reflex response that is not transient during the INS. At each NS, the direct response 202 peaks below the initial baseline 201 followed by a reflex response 204 that peaks above baseline 201 followed by a recovery 203 back toward baseline 201. However this recovery does not return to baseline 201 before the next NS. As a result of the incomplete reflex response recovery between successive NS, the subsequent signal baseline 206 progressively shifts higher above the initial baseline 201 after each NS of the INS. It is believed the effect of non-transient reflex responses accumulating over repeated stimulations during INS may be undesirable in many clinical applications of neural stimulation FIG. 2D illustrates a period of INS similar to FIG. 2C, except the stimulation parameters have been adjusted to cause the reflex response 204 to return to the initial baseline 201 between successive NS. This illustrates a reflex response that is transient during the INS. Some of the parameters that can be adjusted include, but are not limited to, the magnitude and duration of the stimulation pulse, the location of the stimulation, and the timing and duration of bursts of neural stimulation in a therapy that intermittently delivers neural stimulation bursts. Some embodiments modulate efferent and/or afferent nerve activity. The desired parameters can be selected based on empirical data, or based on a neural stimulation test routine performed at the time of the implantation of a neural stimulation device. For example, studies have indicated that neural stimulation bursts delivered using a nerve cuff electrode to the vagus nerve in the cervical region, where the duration of the burst is approximately 10 seconds and the bursts are repeated once every minute, and where the electrical pulses have approximately a 1 mA current and a frequency of about 20 Hz, provide a desirable transient direct and reflex response to the neural stimulation.

Figure 3:
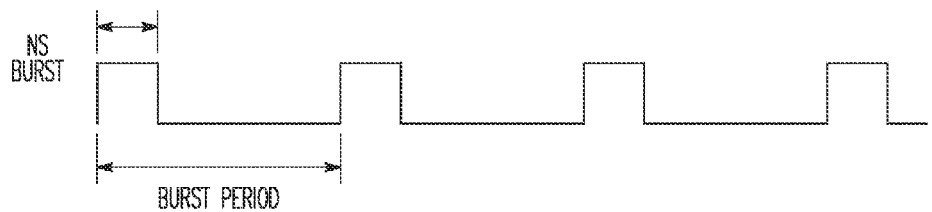
FIG. 3 illustrates a train of neural stimulation bursts used to provide parasympathetic stimulation.

FIG. 3 illustrates a train of neural stimulation bursts used to provide parasympathetic stimulation. Each burst includes a plurality of pulses (not illustrated) within the burst. In the illustration, each burst has an equal duration (e.g. on the order of 10 seconds) and the bursts are separated by a burst period (e.g. on the order of one minute). The duration and/or burst period may be adjusted during the therapy to adjust the therapy dose and the transient evoked response. The dose and transient evoked response may be adjusted by changing the amplitude, pulse frequency, and/or pulse width of the neural stimulation pulses within the burst.

Figure 4A:
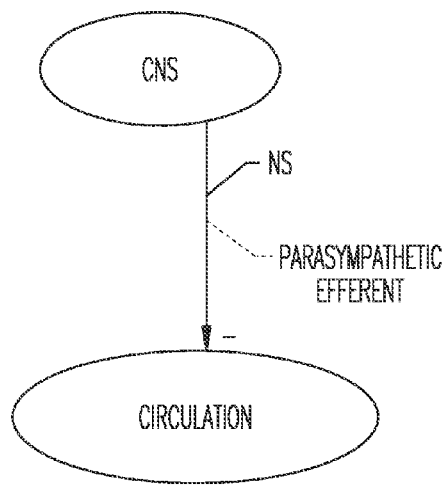
FIGS. 4A, 4B, 5A and 5B illustrate applications of the neural stimulation illustrated in FIG. 3 to a target to elicit an ANS effect on heart rate (HR) or blood pressure (BP).
Figure 4B:
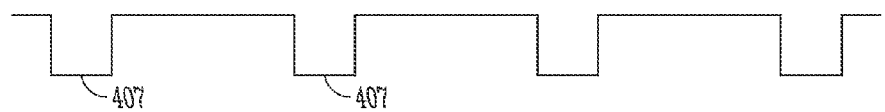
Figure 5A:
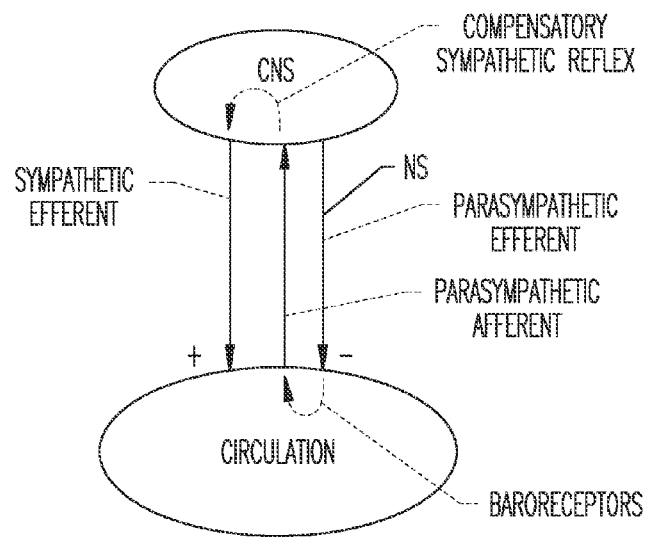
Figure 5B:
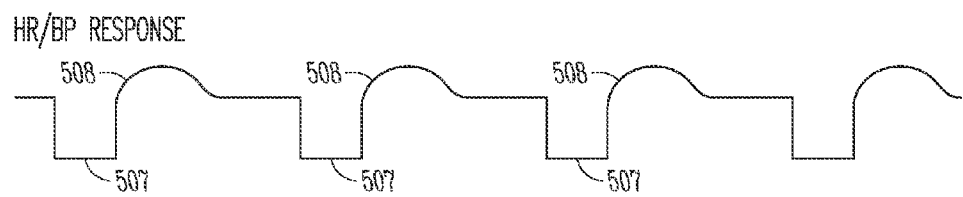

FIGS. 4A, 4B, 5A and 5B illustrate applications of the neural stimulation illustrated in FIG. 3 to a target to elicit an ANS effect on heart rate (HR) or blood pressure (BP). Negative-going waveforms illustrated in FIGS. 4B and 5B indicate a decrease in HR or BP, such as expected from parasympathetic stimulation, while positive-going waveforms indicate an increase in HR or BP, such as expected from sympathetic stimulation. FIGS. 4A and 4B illustrate stimulation parameters adjusted to elicit a transient direct parasympathetic effect. FIGS. 5A and 5B illustrate stimulation parameters adjusted to elicit transient direct parasympathetic and transient reflex sympathetic effects.

FIG. 4A illustrates an efferent parasympathetic target, and FIG. 4B illustrates a direct response on circulation (e.g. lowered heart rate or blood pressure) to the parasympathetic stimulation pulse train, as illustrated in FIG. 3, at an efferent parasympathetic target, as illustrated in FIG. 4A. Action potentials in afferent nerves travel toward the central nervous system (CNS), and action potentials in efferent nerves travel away from the CNS. As illustrated in FIG. 4B, the direct response 407 attributed to the selective stimulation of the efferent pathway follows the time course of neural stimulation pulses and returns to baseline between stimulation bursts (i.e., it is transient). The efferent stimulation in this example results in a small direct response in HR or BP that does not elicit a measurable reflex response, as indicated by immediate return to baseline of the response following termination of the stimulation burst.

FIGS. 5A and 5B illustrate an efferent parasympathetic target with an afferent parasympathetic pathway carrying signals from the target to the CNS and an efferent sympathetic pathway from the CNS carrying reflex stimulation to the target. FIG. 5B illustrates a direct and reflex response of the circulation (e.g., heart rate decrease then increase or blood pressure decrease then increase) to the parasympathetic stimulation pulse train, as illustrated in FIG. 3, at an efferent parasympathetic target as illustrated in FIG. 5A. As illustrated in FIG. 5B, the selective stimulation of the efferent pathway provides a direct response 507 and a reflex response 508. In this example, the efferent stimulation elicits a reflex response when baroreceptors in FIG. 5A respond to the lowered HR or BP, sending impulses to the CNS in the afferent nerve illustrated in FIG. 5A and thereby eliciting a compensatory sympathetic reflex that increases HR and BP via impulses conveyed from the CNS in the sympathetic efferent pathway illustrated in FIG. 5A. As illustrated in FIG. 5B, the direct response ends quickly after the end of the stimulation burst, whereas the reflex response continues measurably after the end of the stimulation burst, and both direct and reflex responses return to baseline before the next stimulation burst (i.e., they are transient).

The present subject matter is not limited to a particular mechanism, but rather monitors responses to ANS modulation to verify and, in some embodiments, control the evoked direct and reflex responses of the neural stimulation to be transient. For example, the present subject matter provides a means to monitor or measure INS responses, as a way of promoting balanced transient direct and reflex effects and/or promoting the avoidance of undesirable physiological effects. For example, the present subject matter can measure the magnitudes of direct and reflex responses and detect their washout before subsequent stimulation, and the ANS can be stimulated to allow the direct and reflex responses of neural stimulation to be transient.

Monitoring ANS Response to Intermittent NS Bursts

Figure 6A:
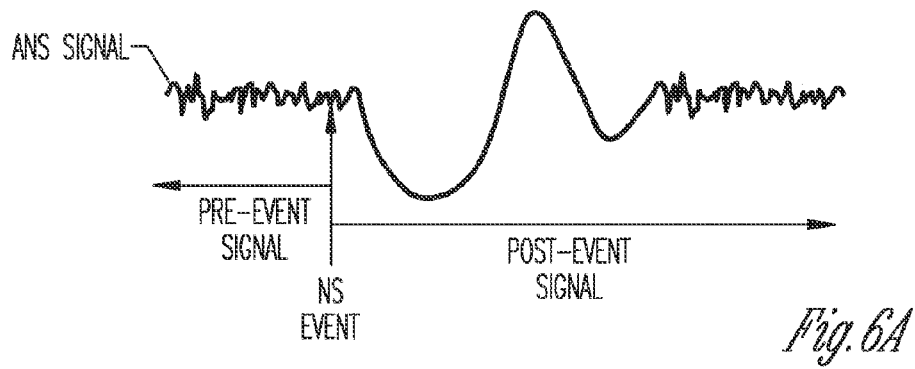
FIGS. 6A-6C illustrate various embodiments for monitoring a response to an intermittent NS burst.
Figure 6B:
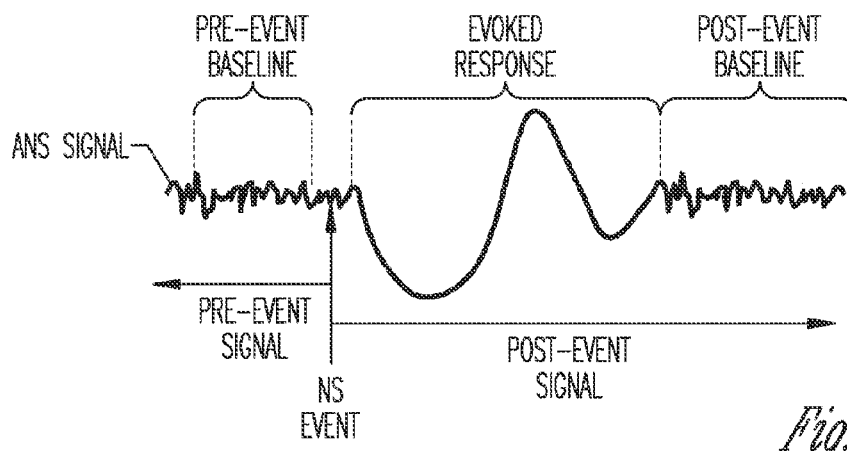
Figure 6C:
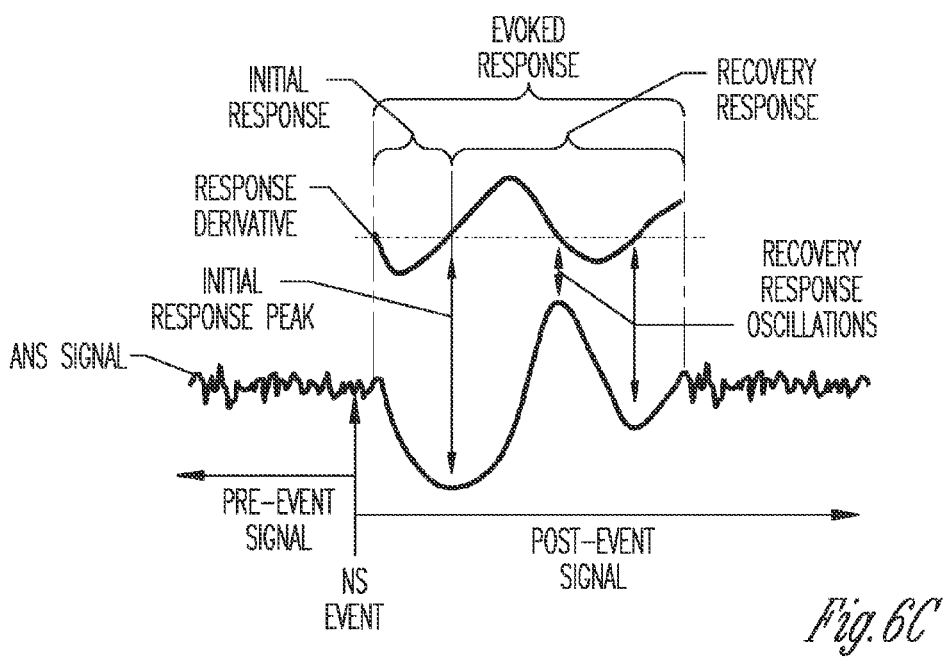

FIGS. 6A-6C illustrate various embodiments for monitoring a response to an intermittent NS burst. Multiple bursts can be analyzed, according to various embodiments. Each figure illustrates one neural stimulation burst among a plurality of INS stimulation bursts of a programmed NS therapy. The NS burst includes a plurality of NS pulses that are preceded and followed by a time without NS pulses. In one embodiment illustrated in FIG. 6A, an ANS signal is monitored over time and marked with the NS event, which is a time point with a fixed offset from the start of the NS burst. The NS event offset from the NS burst start may be a zero offset, a negative offset, or a positive offset depending on various signal analysis embodiments, although a zero offset is preferred. The NS event divides the ANS signal into a Pre-Event Signal and a Post-Event Signal. The pre-event signal and the post-event signal can be compared using various signal analysis embodiments, as detailed below, to determine which portion of the post-event signal is correlated to the NS event. Some embodiments select INS therapy parameters to provide that the post-event signal becomes uncorrelated to the NS event before the next intermittent NS burst, making the response to NS transient. In one embodiment illustrated in FIG. 6B, the pre-event signal contains a pre-event baseline and the post-event signal contains an evoked response and a post-event baseline. In this example, the INS therapy parameters are selected so that the pre-event signal is not measurably influenced by (e.g., not correlated to) the immediately preceding NS burst during the pre-event baseline. The pre-event baseline interval can begin anytime before the NS event when the pre-event signal is uninfluenced by the preceding NS and can end anytime before or at the NS event. The evoked response is a post-event signal correlated to the NS event that is measurably different from the pre-event baseline signal. The difference can be determined as detailed below (e.g. signal averaging and boxcar testing). The evoked response interval begins when the post-event signal deviates measurably from the pre-event baseline signal, and it ends when the signal becomes measurably similar to the pre-event baseline signal. The post-event baseline is that portion of the post-event signal following the evoked response when the signal is similar to the pre-event baseline signal. Some embodiments select INS therapy parameters to provide a post-event baseline, making the evoked response to each NS burst transient. In one embodiment illustrated in FIG. 6C, the evoked response is analyzed to detect and measure components representative of the direct and reflex responses to NS. In this example, peaks in the evoked response are detected by zero-crossings in the first derivative of the evoked response signal. The initial response peak generally results from a direct response to NS. The interval from the start of the evoked response to the initial response peak is the initial response, which generally is representative of the direct response of NS. After the response peak, the evoked response recovers toward baseline and can oscillate above and below baseline before recovering to baseline levels. Measurable recovery response oscillations generally result from a reflex response to NS. The interval from the end of the initial response to the end of the evoked response is the recovery response, which generally is representative of the reflex response of NS. Recovery response oscillations indicate the occurrence and nature of the reflex response. In some embodiments INS therapy parameters are selected to balance direct and reflex response magnitudes and/or durations. In some embodiments parameters are selected to maximize or minimize either or both of the direct and reflex response magnitudes and/or durations. Some embodiments maximize the direct response and minimize the reflex response, while others minimize the direct response and maximize the reflex response. Some embodiments try to evoke a pattern of direct and reflex responses.

Figure 7:
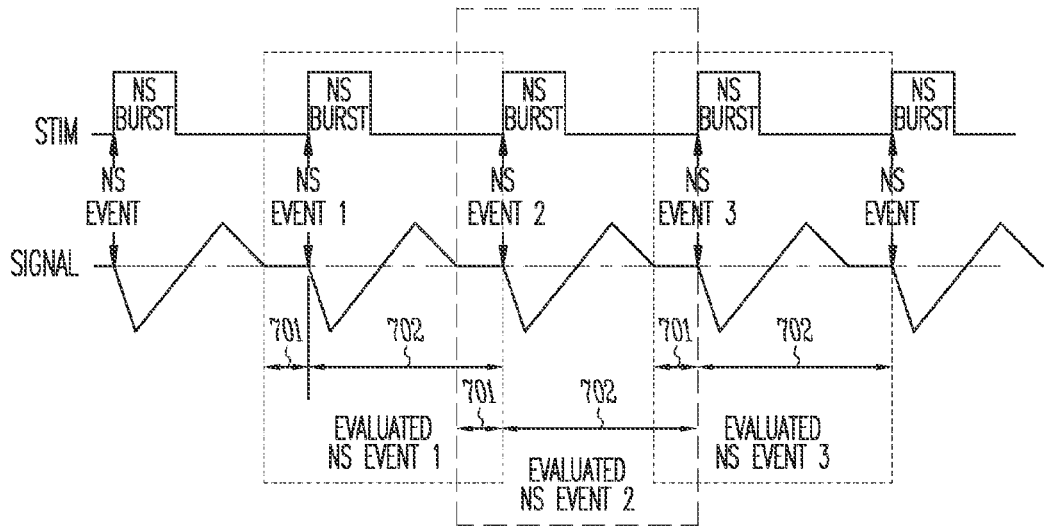
FIG. 7 illustrates various embodiments for monitoring a response to an intermittent NS therapy.

FIG. 7 illustrates various embodiments for monitoring a response to an intermittent NS therapy. The figure illustrates a programmed NS therapy that includes a plurality of intermittent NS stimulation bursts depicted in the top trace "STIM". Each NS burst includes a plurality of NS pulses (not shown), and successive NS bursts are separated by a time without NS pulses. This figure also illustrates the evaluation of the ANS response depicted in the bottom trace "SIGNAL" to three successive NS bursts tagged by NS Event markers 1, 2 and 3, each of which is a fixed offset from the start of its corresponding NS burst. Various embodiments evaluate the ANS response to all NS bursts in the therapy. Some embodiments evaluate the ANS response to an NS burst in response to a device command (e.g. according to a schedule or in response to a detected event) or a command from a physician. FIG. 7 illustrates that each evaluated NS event includes a pre-event signal 701 and a post-event signal 702. To evaluate a transient response, the pre-event signal 701 is selected to start after the end of the response correlated to the immediately preceding NS burst, and the post-event signal 702 is selected to end before the immediately following NS event marker. As illustrated in FIG. 7, the post-event signal 702 of one evaluated NS event can overlap with the pre-event signal 701 of a following evaluated NS event. In evaluating a NS event, some embodiments only monitor the post-event signal of the burst. Other embodiments monitor the pre-event signal before the NS event and monitor the post-event signal after the NS event. Various embodiments use the pre-event signal before the NS event to provide a baseline response. In evaluating a NS event, some embodiments monitor the pre-event baseline before the NS event and monitor the evoked response to the burst. Various embodiments evaluate components of an evoked response corresponding to the direct and reflex response to NS in an effort to evoke a specific pattern of direct and reflex response, for example, to balance the transient physiological effects of the NS therapy.

Figure 8:
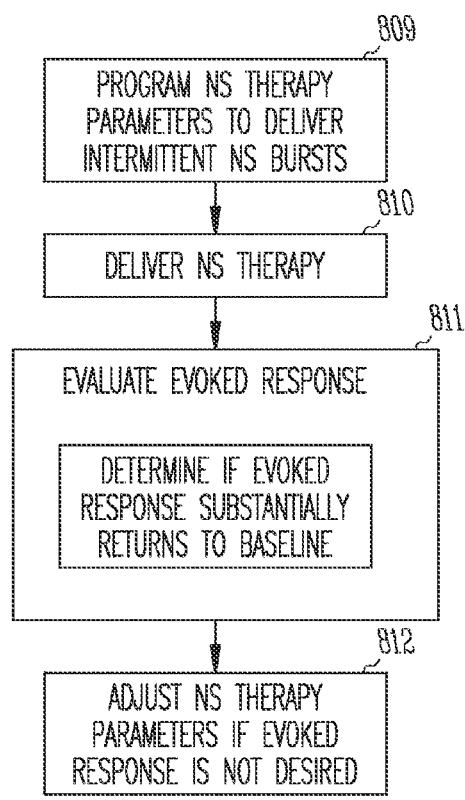
FIGS. 8 and 9 illustrate various methods for delivering neural stimulation therapy and evaluating an evoked response to intermittent NS pulses, according to various embodiments.
Figure 9:
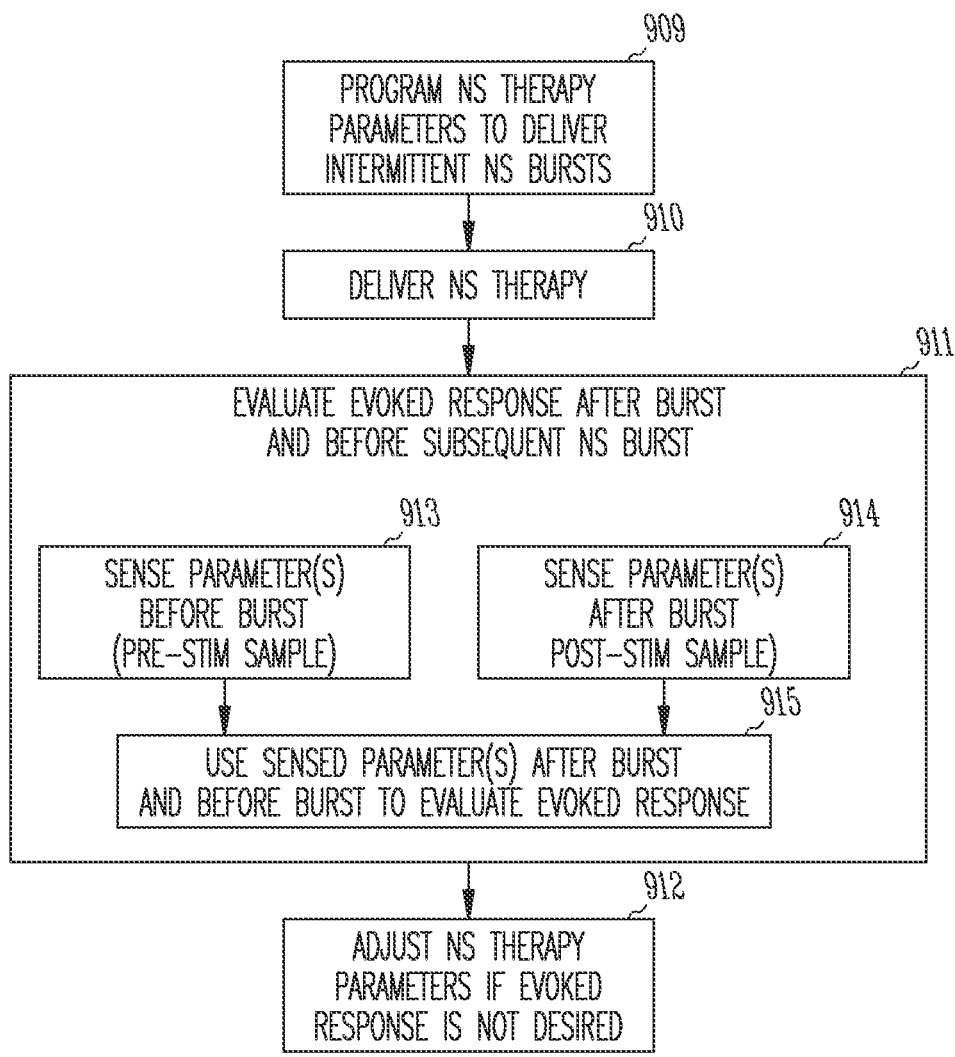

FIGS. 8 and 9 illustrate various methods for delivering neural stimulation therapy and evaluating an evoked response to intermittent NS pulses, according to various embodiments. In the embodiment illustrated in FIG. 8, therapy parameters to deliver intermittent NS bursts are programmed into an implantable medical device at 809. At 810, the programmed NS therapy is delivered to an ANS target to modulate the ANS. The programmed therapy includes bursts of NS pulses. At 811, the evoked response is evaluated. For example, some embodiments determine if the evoked response substantially returns to a baseline before the next burst. In some embodiments, the post-event signal that is correlated to a NS event with a defined time offset from each NS burst is evaluated, and at 812, the NS therapy parameters are adjusted if the correlated signal is not as desired, e.g., if it is not transient or not balanced or otherwise unacceptable as described herein. In the embodiment illustrated in FIG. 9, therapy parameters to deliver intermittent NS bursts are programmed into an implantable medical device at 909. At 910, the programmed NS therapy is delivered to an ANS target to modulate the ANS. The programmed therapy includes bursts of NS pulses. At 911, an evoked response in the post-event signal correlated to a NS event with a defined time offset from each NS burst and deviating from the pre-event signal is evaluated; and at 912, the NS therapy parameters are adjusted if the response is not as desired, e.g., if it is not transient or not balanced or otherwise unacceptable as described herein. In the illustrated embodiment, the evaluating the evoked response 911 includes sensing one or more parameters in the pre-event signal (also referred to as a pre-stimulation sample) 913 and sensing the one or more parameters in the post-event signal (also referred to as a post-stimulation sample) 914. At 915, the pre-stimulation sample and the post-stimulation sample are compared to evaluate the evoked response.

There are a number of methods that may be used to characterize and monitor the ANS response to the stimulation. For example some embodiments confirm that the evoked response is transient as it returns to a baseline before a subsequent neural stimulation burst, some embodiments determine the duration of the response, some embodiments determine the area under the response curve, some embodiments automatically search for an evoked response goal, some embodiments use sensors from other devices to confirm the response, and some embodiments optimize a compensatory reflex-mediated effect.

Some evoked responses are managed to be transient because they are unwanted side-effects of the NS at a level necessary for effective treatment outcomes (e.g. bradycardia, discomfort, ancillary muscle stimulation, and the like). Some evoked responses are managed to optimize or otherwise improve the effectiveness of the NS therapy, and some embodiments are managed to oscillate parasympathetic and sympathetic responses to optimize or otherwise improve the effectiveness of the NS therapy.

Some embodiments use signal averaging to detect evoked responses in the presence of background signal fluctuation. Signals from repeated INS stimulation bursts are aligned to a defined NS event and averaged over the repeated samples, which minimizes the uncorrelated background fluctuations and extracts the correlated evoked response signal. INS therapy parameters then can be adjusted to ensure that the evoked response is transitory and has an acceptable pattern. Examples of this technique are presented below.

Some embodiments use Fourier analysis to detect and measure evoked responses. Fourier decomposition of the signal data time-series can determine the frequency spectrum of the signal and detect when oscillations of specific frequency are present and measure their power. These indicators can be used to optimize and control the transient response.

Some embodiments use autocorrelation to determine the duration of the transitory response. Autocorrelation of the background fluctuating signal (without NS) will have some baseline value. However, the signal fluctuation caused by NS will have a higher (different) autocorrelation value for the period when the signal is affected by the NS. The signal before and following an NS event is subject to autocorrelation over some sample duration period. The signal before the stimulation and after the transient response has receded to background should have an autocorrelation value reflecting only random changes in the signal. The signal change resulting from the NS event will have a higher autocorrelation value compared to autocorrelation of the baseline preceding the simulation. The end of the NS transient event is detected when autocorrelation of the signal following the NS event declines to the pre-NS baseline value.

Some embodiments use cross-correlation to determine the duration of the transitory response. A random time interval (period) of the signal has a low correlation when cross-correlated with another random time interval of the signal when the signal fluctuations are due to randomly varying factors. However two time intervals, each following a NS event, are expected to have highly correlated values because the signal should fluctuate similarly as part of the NS response. The signal following the NS event can be divided into a series of sequential time intervals (e.g. i=1, 2, . . . n)

of a fixed duration (the duration being set according to expectations about how long the transitory response will last). The cross-correlation between corresponding intervals after different NS events [e.g., E(1,i), E(2,i), ... E(N,i)] are expected to be highly correlated for intervals during which there is in fact an NS-generated signal response, and are expected to be uncorrelated when intervals are compared that occur after the NS response has diminished to background levels. The last interval exhibiting significant correlation would be the end of the transient response. The signals could be pre-filtered or averaged to remove non-stationary fluctuations before correlation, for example, to remove slow frequency drifts in signal levels.

Some embodiments use template matching techniques to detect and measure particular patterns of evoked response. Templates may be stored in memory in an implantable neural stimulator. Templates can be based on whole signals or a collection of partial signals. Templates can be based on a characteristic set of features extracted from the signals, for example, the relative times of peak values, number of baseline (zero) crossings, signal slopes, and the like. Template matching can use any available method known in the art. An example is correlation of the template and the signal. Signals can be pre-processed by filtering and averaging, etc, before template matching.

Some embodiments measure the area under the curve as a way to determine when a balanced or otherwise desirable response is obtained. Some embodiments find the end of a transient response (i.e., the duration/period of the transient response) by measuring the area under the curve cumulatively from the NS event to each time point following the NS event until a time point is found where the cumulative area approaches zero (or another defined value). For example, the stimulation intensity/duration parameters are adjusted until the area under the curve for a tracked physiological variable (e.g. BP or HR) during a defined transient response period approaches a net of zero or some other defined net value.

Some embodiments perform an automated search over a range of neurostimulation parameters for an evoked response goal. For example, various embodiments program and constrain the automated search behavior to be for specified parameters alone or in combination over a defined parameter range, a defined search schedule, or a defined success/failure criteria. Some example search methods are parameter ramps (e.g., amplitude ramp, a stimulation duration ramp), hill climbing techniques, simulated annealing, and other algorithmic search techniques. For example, NS burst duration and burst interval, and/or stimulation pulse intensity and pulse frequency may be varied during a search. Different stimulation locations (with multi-electrode configurations) and stimulation waveforms (with single or multi-electrode configurations) may be varied to change the axon (neural pathway) sets that are captured, to allow search over different neural pathways for an optimal transient response.

The present subject matter is designed to allow NS to be configured to achieve long-term clinical treatment effects (outcomes) while avoiding or otherwise controlling specific transient response effects. The NS treatment effects (outcomes) can be measured by standard clinical indicators of disease state. For example, for cardiovascular applications, treatment success can be measured by biomarkers (BNP, ANP, TNF, SERCA, cardiac troponins, creatine kinase, MMPs, TIMPs, interleukins, plasma NE, C-reactive protein, etc.), cardiac functional measurements (minimum, maximum, and mean HR, HR variability, ejection fraction, valve regurgitation, stroke volume, systolic and diastolic BP, cardiac chamber systolic and diastolic pressures, contraction synchrony and pattern, etc.), cardiac structural measures (end-diastolic and end-systolic volumes, vessel patency/occlusion, etc), clinical measures (patient weight, six-minute walk distance, peak $VO_2$, hospitalization frequency, MI events, quality of life scores, etc.). These clinical measures of the outcome of the treatment are all expected to be apparent over clinical recovery time periods, typically, weeks or months. Measures of a clinical response are distinct from measures of a NS evoked response, which various embodiments described herein actively manage to be transient.

One of the monitored physiological event responses to the neural stimulation, according to various embodiments, is an oscillatory response corresponding to a direct effect of the neurostimulation followed by an opposite compensatory reflex-mediated effect. Some embodiments improve or optimize this oscillatory response. For example, various embodiments maximize the peak of the direct NS response, the reflex response, or both. Various embodiments maximize the duration of the direct NS response, reflex response or both. Various embodiments minimize the duration of the direct NS response, reflex response or both. Various embodiments perform some combination of maximizing and minimizing the direct NS or reflex response peak and/or duration. Some embodiments measure oscillations by detecting zero crossings in the first derivative of the response, in some cases after performing filtering to remove high frequency oscillations. Some embodiments for generating and improving or optimizing a response select the stimulation parameters dependent on the baseline HR or baseline BP or other baseline physiological measure. For example, if baseline HR is high, neural targets are selected to increase parasympathetic tone to decrease HR and provide a desired direct and or indirect HR response. If baseline HR is low, neural targets are selected to increase sympathetic tone to increase HR and provide a desired direct or indirect HR response.

Some embodiments deliver NS while controlling the evoked response of HR or BP (or other physiological variable) to be below a threshold level. For example, this permits NS to be delivered while ensuring there is no change or only an acceptably low change in HR, BP or other monitored physiological parameter that is subject to transient response control. A therapeutically effective NS level can be determined by detecting specific evoked responses known to be associated with an effective level of stimulation. For example, vagal stimulation configured to evoke laryngeal vibration may indicate a minimum effective therapeutic level (i.e. a minimum or lower range of levels that stimulate the A fibers of the vagus), and it can be measured by the device or physician to ensure the device is set to a minimally effective level (i.e., that the device is still working by continuing to deliver the lower range of therapeutically-effective stimulation). Then the device may increase the level of stimulation to maximize the therapy while controlling the transient response of monitored physiological variables (i.e., controlling unwanted transient side-effects or adjusting a transient response for optimal therapy). An example of controlling the evoked response is discussed in U.S. patent application Ser. No. 12/487,266 filed Jun. 18, 2009 and entitled Systems and Methods for Delivering Vagal Nerve Stimulation, which is hereby incorporated by reference in its entirety.

Devices and Systems

Figure 10:
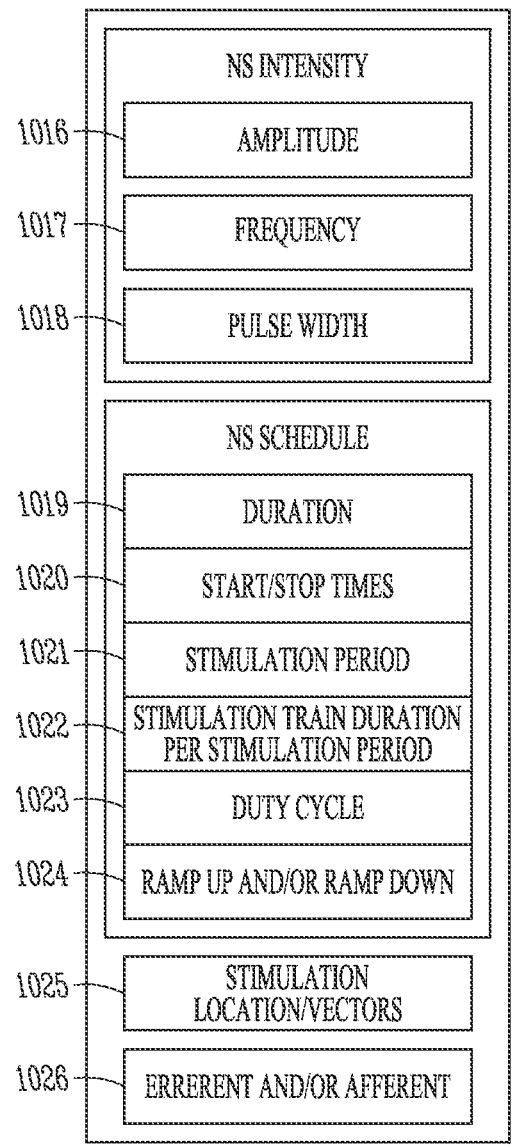
FIG. 10 illustrates some examples of programmable parameters that may be used and modified based on a detected evoked response to the intermittent neural stimulation.

FIG. 10 illustrates some examples of programmable parameters that may be used and modified based on a detected evoked response to the intermittent neural stimulation. The programmable parameters can include parameters used to adjust the intensity of the neural stimulation therapy, such as amplitude 1016, frequency 1017, pulse width 1018. Some embodiments adjust the neural stimulation schedule to adjust the neural stimulation intensity. Examples of schedule parameters include therapy duration 1019 (e.g. how many minutes the INS therapy protocol is delivered), start/stop times 1020 (e.g. when to start or stop the INS therapy protocol), stimulation period 1021 (e.g. the burst interval of the INS therapy protocol), stimulation train duration per stimulation period 1022 (e.g. the burst duration of the INS therapy protocol), duty cycle 1023 (e.g. the stimulation duration/stimulation period of the INS therapy protocol), and a ramp up and/or ramp down 1024 for the intensity of the stimulation burst. Some embodiments are designed with the ability to operationally position a plurality of electrodes near the neural pathway to stimulate different locations along the neural pathway to initiate an action potential at these different locations along the neural pathway, as generally illustrated at 1025. Some embodiments change where the nerve is stimulated to change the distance that the action potential has to travel before inducing a response, and thus changes the timing of the response induced by the action potential for a direct response or a reflex response. Some embodiments control whether an efferent or afferent pathway is being stimulated, as illustrated generally at 1026.

The neural stimulation delivered during the duty cycle can be delivered using a variety of neural stimulation techniques, such as stimulation that uses electrical, ultrasound, thermal, magnetic, light or mechanical energy. Electrical neural stimulation is used in this document as an example of neural stimulation. In electrical stimulation, for example, a train of neural stimulation pulses (current or voltage) can be delivered during a duty cycle of stimulation. Stimulation pulse waveforms can be square pulses or other morphologies. Additionally, the stimulation pulses can be monophasic or biphasic pulses.

Figure 11:
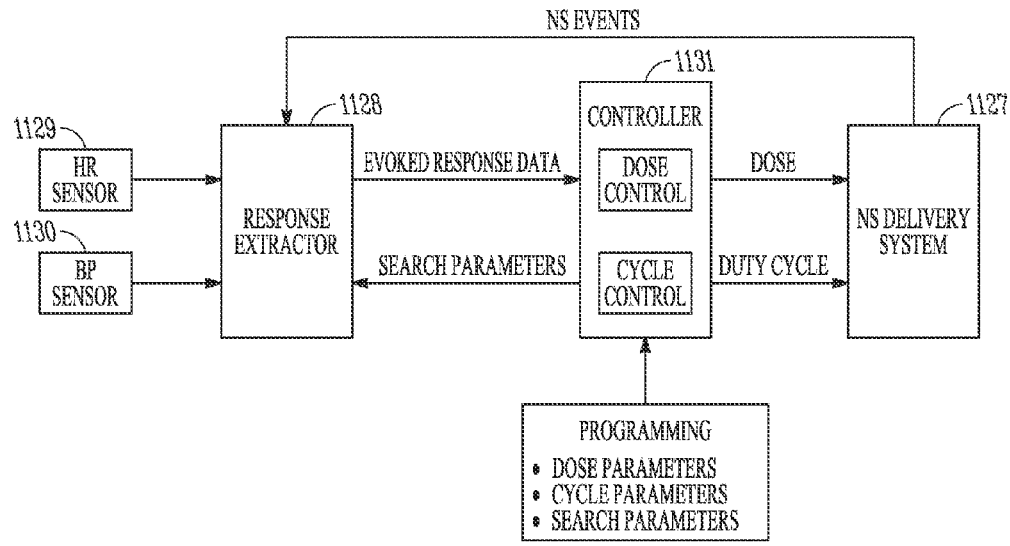
FIG. 11 illustrates a system embodiment configured to extract an evoked response and control stimulation using the extracted response.

Various embodiments control neural stimulation to provide controlled, transient changes in the HR, BP and other physiological activity following intermittent neurostimulation events. The following examples are illustrated using heart rate and blood pressure signals and targets. Heart rate and blood pressure are non-exclusive examples. As is known in the art, other physiologic parameters are affected by ANS activity. The present subject matter may be implemented using other physiological signals and targets. FIG. 11 illustrates a system embodiment configured to extract an evoked response and control stimulation using the extracted response. Various device embodiments include a neural stimulation delivery system 1127 (also referred to as a neural stimulator), a response extractor 1128 that is capable of providing feedback from sensors (e.g. HR sensor 1129 and/or BP sensor 1130, and others), and a controller 1131. The neural stimulator is configured to directly or reflexively modulate heart rate and/or blood pressure, for example. The response extractor extracts a representation of the evoked response by determining how the heart rate and/or blood pressure response is correlated with a given intermittent neurostimulation, and then determines parameters of the response, such as overall duration, direct and reflex response durations and magnitudes, and others. The controller is configured to modulate the neurostimulation dose and/or duty cycle to provide an evoked response that is transient and/or to achieve a pre-determined evoked response pattern.

Thus, some embodiments limit the HR or BP responses evoked by intermittent NS to be transient in nature, where the HR or BP returns to the baseline before the next stimulation burst is delivered. That is, the HR and BP will return on average to pre-stimulation levels between successive intermittent stimulations. This does not preclude long-term progression in HR or BP, which may be a therapeutic goal of chronically-applied NS. The difference is that transient changes occur on the order of the intermittent NS duty cycle (e.g., minutes), while long-term therapeutic changes occur on the order of chronic clinical changes (e.g., days or months). Other embodiments similarly control other physiological targets and signals.

HR sensors can be used to record HR time series signals, and BP sensors can be used to record BP time series signals. A neural stimulation (NS) event (e.g., an intermittent burst of given amplitude, duration, location, polarity, etc.) may evoke a perturbation in HR or BP that has a predictable and repeatable pattern and duration, referred to herein as the evoked response. Time series decomposition can extract the evoked response that is correlated with intermittent NS events of a given dose. In particular the duration of the evoked response can be determined by determining the length of time the correlated perturbations due to a NS event persist. The duration of this evoked response is the time required for changes in HR or BP due to the NS event to wash out, that is, return to baseline. Once this is determined by a response extractor for a given NS dose, the INS duty cycle can be adapted by the controller to ensure that any changes in HR or BP due to intermittent NS events are transient. This avoids clinical risks that may be caused by persistent adverse changes in HR or BP during NS therapy (e.g., causing excessive bradycardia in heart failure patients). Also the pattern of the evoked response can be analyzed to determine and measure direct and reflex response components. For example as illustrated in FIG. 6C, the initial response to the NS burst can be detected by the initial response peak, which generally corresponds to the direct response. This is followed by the recovery response, when the initial response recovers to baseline, either directly or with one or more response oscillations. The presence of oscillations in the recovery response is an indication of reflex responses. The magnitudes of the direct and reflex responses can be estimated by their corresponding response peaks detected as zero-crossings in the response first derivative, and their durations can be estimated by the interval between the first derivative peaks corresponding to the slope changes on either side of their response peaks. The controller may control features of the stimulation protocol to control the magnitude, duration, and other patterns of the direct and reflex response to the stimulation.

The effect of the neural stimulation on HR or BP is controlled by the NS dose, which consists of a complex set of variables, including electrode design, stimulation site, pulse amplitude, width and phase, pulse burst duration and pattern, stimulation timing, and the like. The selection of NS dose depends on the therapeutic application of the device. In some applications, the NS dose may be selected to decrease or increase HR or BP transiently by directly stimulating neural pathways that control HR or BP. This in turn may result in compensatory reflex changes in HR or BP after the NS event ends. In such cases, the NS event may cause an oscillation of HR or BP that lasts for several seconds or minutes. These are oscillatory evoked responses. They may be preferred in some applications of the device to deliver a combination of directly stimulated and reflex changes in ANS activity. By altering the NS dose, the device can control the magnitude, pattern, and duration of the HR or BP evoked responses. A device response extractor can measure these evoked response parameters to be used by a controller to adapt the NS dose to achieve a preferred or optimal evoked response.

HR and BP sensors 1129 and 1130 provide a continuous stream of HR and BP signal data to the response extractor 1128. This data stream can be digitized into a discrete time series for analysis. The response extractor 1128 is notified of each intermittent NS event from the NS delivery system 1127. The response extractor uses these events to process the signal time series to detect correlated responses in the signal following an event. Multiple NS events are analyzed to extract a correlated response from background (uncorrelated) signal fluctuations. The extracted correlated response is then quantified to provide evoked response data, such as response duration, to the controller. The controller 1131 uses these data according to programmed parameters to control the duty cycle and/or the dose of the neurostimulation. For example, the controller may be programmed to adjust the INS interval to be greater than or equal to the duration of the evoked response, thus ensuring that HR or BP responses caused by each NS event return to background levels before the next NS is delivered. The controller may be programmed to adjust the NS dose until the evoked response data match programmed criteria, such as a minimum or maximum duration or a minimum or maximum response level, or many other possibilities. The controller provides search parameters to the response extractor to control its functions. For example, the controller may set search criteria or search windows for the extraction algorithms, or request which evoked response data are to be extracted, among other possibilities.

Figure 12:
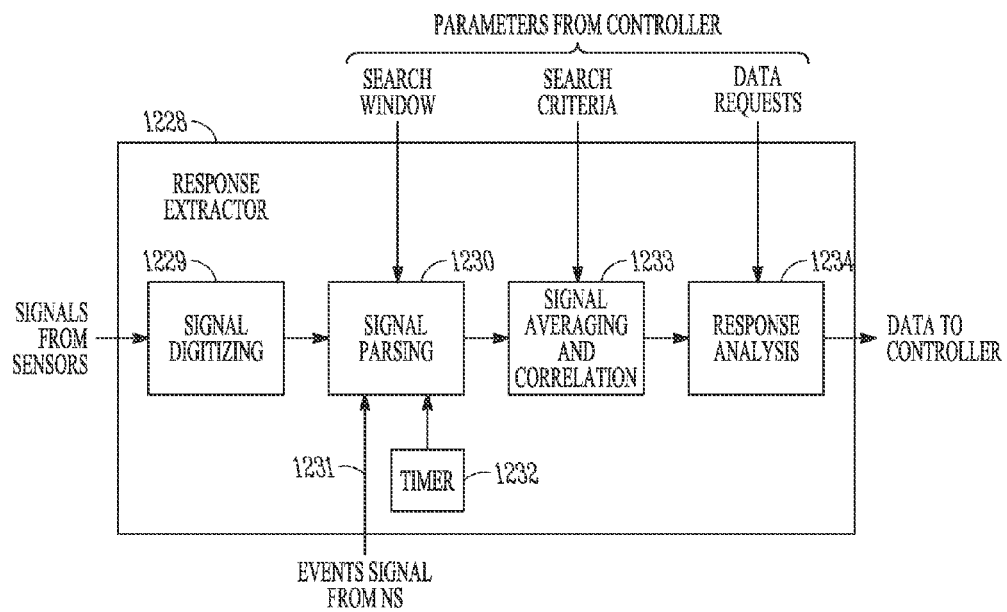
FIG. 12 illustrates an embodiment of the response extractor.

FIG. 12 illustrates an embodiment of the response extractor 1228. Continuous analog signals from the HR or BP sensors are converted to digitized time series at signal digitizing 1229. These in turn are processed by signal parsing 1230 where the time series are parsed into event samples. The time series are parsed into event samples with a temporal sampling window aligned to a NS event, which is a time point defined by a fixed offset (usually zero) from the start of each NS burst. A sampling window may be defined to start a specified time just before a NS event and end a specified delay following a NS event. The event signal 1231 from the NS delivery system and a timer 1232 may be used in providing the sampling window. The signal data inside the sampling window constitute an event sample. In one application, the sampling window is specified to be somewhat longer than the expected evoked response time in order to ensure that the entire evoked response is sampled.

Multiple event samples are processed at 1233. For example, some embodiments use signal averaging, and some embodiments use correlation. For example, event samples are processed by signal averaging to extract the event-related signal response (evoked response) from background signal fluctuations. Each event sample is aligned in time at the NS event (e.g., the time base of each sample time series is shifted so that time zero occurs at the NS event time). Then the signal values of all the samples at each time point are averaged. An equation for this is as follows: For all data points t in each event sample E[s] in the set of S samples, $$E_{Avg}[t] = \frac{1}{S}\sum_{s=1}^{S} E[s, t]$$

where $E_{Avg}$ is the averaged response time series. This averaging subtracts background signal fluctuations from the signal perturbations correlated with the NS event. The result is an averaged time series representing the evoked response. The evoked response is passed to the response analysis 1234 for feature extraction. The evoked response is processed to determine the response duration, according to some embodiments. This can be accomplished, for instance, with a baseline boxcar search. A baseline search box is created by determining the range of signal fluctuation within a time window just before the expected start of the evoked response associated with the NS event, for example, in the pre-event signal. That is, the search box will contain all values of the signal during a fixed length period prior to the start of the evoked response. Then the evoked response is searched for the first point in time when the signal falls within the search box range for the entire search box duration. Parameters for this search can be set by the controller to establish, for example, duration of the search box, search tolerances and limits, search starting point, and many other possibilities.

Figure 13:
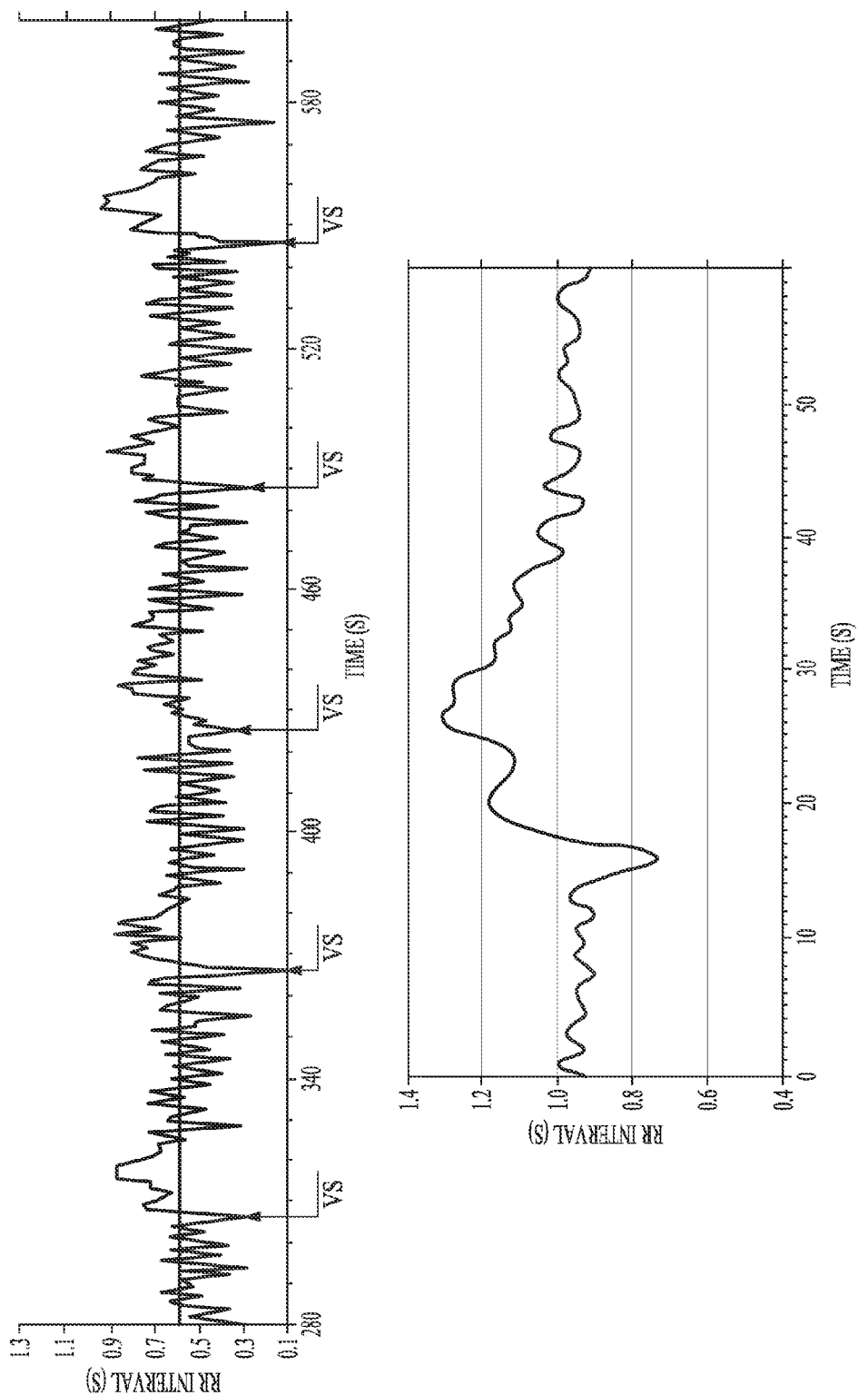
FIG. 13 illustrates an example of signal averaging measurements used in various embodiments, where the first panel illustrates the measurements of systolic pressure during vagal stimulation cycles and the second panel illustrates signal averaging of 30 one minute samples of signal data.

FIG. 13 illustrates an example of signal averaging measurements, where the first panel illustrates the measurements of systolic pressure during vagal stimulation cycles and the second panel illustrates signal averaging of 30 one minute samples of signal data. The top panel is a real-time recording of BP signals where neuro stimulation events are delivered at the arrows labeled VS. There is a background oscillation in the signals that masks the signal changes correlated with the NS events. The bottom panel is the evoked response resulting from signal averaging 30 one minute samples of signal data aligned to the NS event (VS). The background oscillation in the signals is substantially reduced, revealing the average evoked response. This evoked response consists of an initial peak decrease in BP (representative of the direct response) followed by two peak increase oscillations in BP (representative of multiple reflex responses) and recovery to pre-stimulation baseline levels before the next stimulation (by around 40 seconds on the recording).

Figure 14:
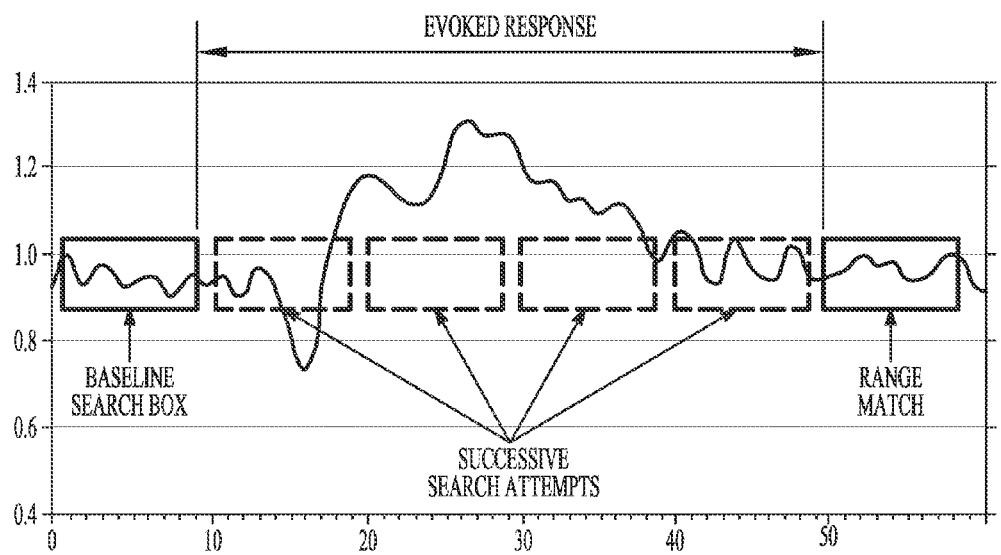
FIG. 14 illustrates an example of using a boxcar search, according to various embodiments, to find an end of the evoked response to neural stimulation.

FIG. 14 illustrates an example of using a boxcar search to find an end of the evoked response to neural stimulation. A baseline search box is determined to find the signal fluctuation range prior to the neural stimulation event and the estimated evoked response. This search box is swept forward in time through the signal until the signal is within the search box range during the entire search box duration (at the box indicated by Range Match). The point in time when this occurs is the defined end of the evoked response.

Figure 15:
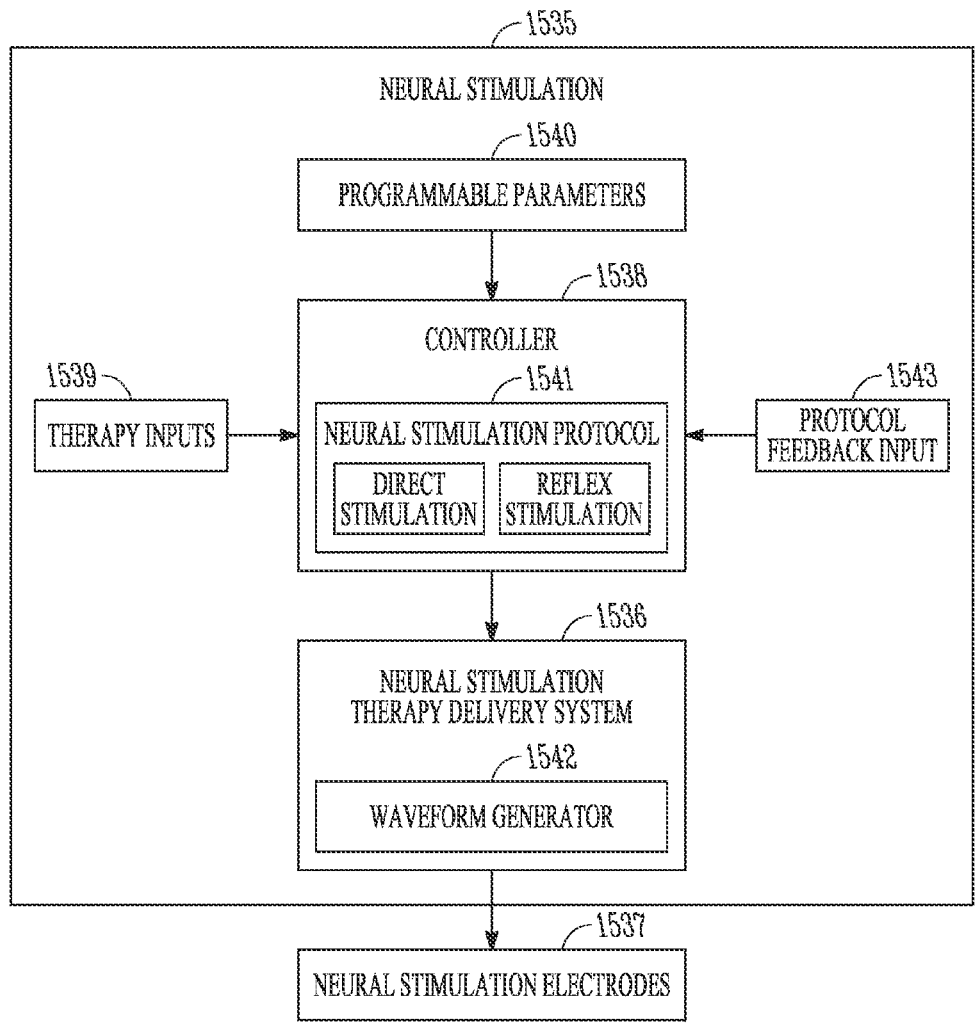
FIG. 15 illustrates a neural stimulator device embodiment adapted to deliver intermittent neural stimulation therapy, according to various embodiments.

FIG. 15 illustrates a neural stimulator device embodiment adapted to deliver intermittent neural stimulation therapy, according to various embodiments. The illustrated device 1535 can be an implantable device or an external device. The illustrated device includes a neural stimulation delivery system 1536 adapted to deliver a neural stimulation signal to the neural stimulation electrode(s) or transducer(s) 1537 to deliver the neural stimulation therapy. Examples of neural stimulation electrodes include nerve cuff electrodes, intravascularly placed electrodes, and transcutaneous electrodes. Examples of neural stimulation transducers include ultrasound, light and magnetic energy transducers. Some embodiments deliver neural stimulation without monitoring the direct response to the stimulation. For example, some embodiments may deliver stimulation without attempting to drive a specific change in heart rate for each stimulation burst, and only limit the change to be transient. Some embodiments deliver therapy using a closed-loop control system, where one or more physiologic parameters, also referred to herein as therapy inputs, are sensed and used as feedback to control the neural stimulation intensity to drive the one or more physiologic parameters to a target value or a target range of values. A controller 1538 receives therapy inputs 1539, and appropriately controls the neural stimulation therapy delivery system 1536 using the therapy inputs 1539 to provide the appropriate neural stimulation signal to the electrode(s)/transducer(s) that results in a desired intensity of neural stimulation, and results in a desired direct and reflex stimulation. The illustrated device includes a memory to store programmable parameters 1540. The controller 1538 implements a neural stimulation protocol 1541 using the programmable parameters to control the waveform generator 1542 of the neural stimulation therapy delivery system 1536. The programmable parameters can be selected to provide the desired direct and reflex response to neural stimulation. The controller 1538 can control the therapy according to programmable therapy dose, duty cycle, and search parameters, as illustrated in FIG. 11. The controller 1538 may include a response extractor, such as generally illustrated in FIG. 12. The illustrated device includes a protocol feedback input 1543, such as may be used to either program the parameters during implant or chronically control the therapy to provide the desired direct and/or reflex response to the neural stimulation. The input 1543 can receive a communication from a device programmer, for use by a physician or patient in changing the programmable parameters based on observed conditions. The input 1543 can receive feedback from physiologic sensors used to monitor transient responses at the beginning and/or end of the neural stimulation train. Examples of such sensors used to provide feedback for the transition protocol include, but are not limited to, heart rate and blood pressure sensors.

Patient management systems can be used to enable the patient and/or doctor to adjust parameter(s) to compensate for undesired transient responses, such as may be sensed by physiologic parameters and output to the patient and/or doctor. The inputs can be provided by computers, programmers, cell phones, personal digital assistants, and the like. The patient can call a call center using a regular telephone, a mobile phone, or the internet. The communication can be through a repeater, similar to that used in Boston Scientific's Latitude patient management system. In response, the call center (e.g. server in call center) can automatically send information to the device to adjust or titrate the therapy. The call center can inform the patient's physician of the event. A device interrogation can be automatically triggered. The results of the device interrogation can be used to determine if and how the therapy should be adjusted and/or titrated to improve the transient response. A server can automatically adjust and/or titrate the therapy using the results of the device interrogation. Medical staff can review the results of the device interrogation, and program the device through the remote server to provide the desired therapy adjustments and/or titrations. The server can communicate results of the device interrogation to the patient's physician, who can provide input or direction for adjusting and/or titrating the therapy.

Figure 16:
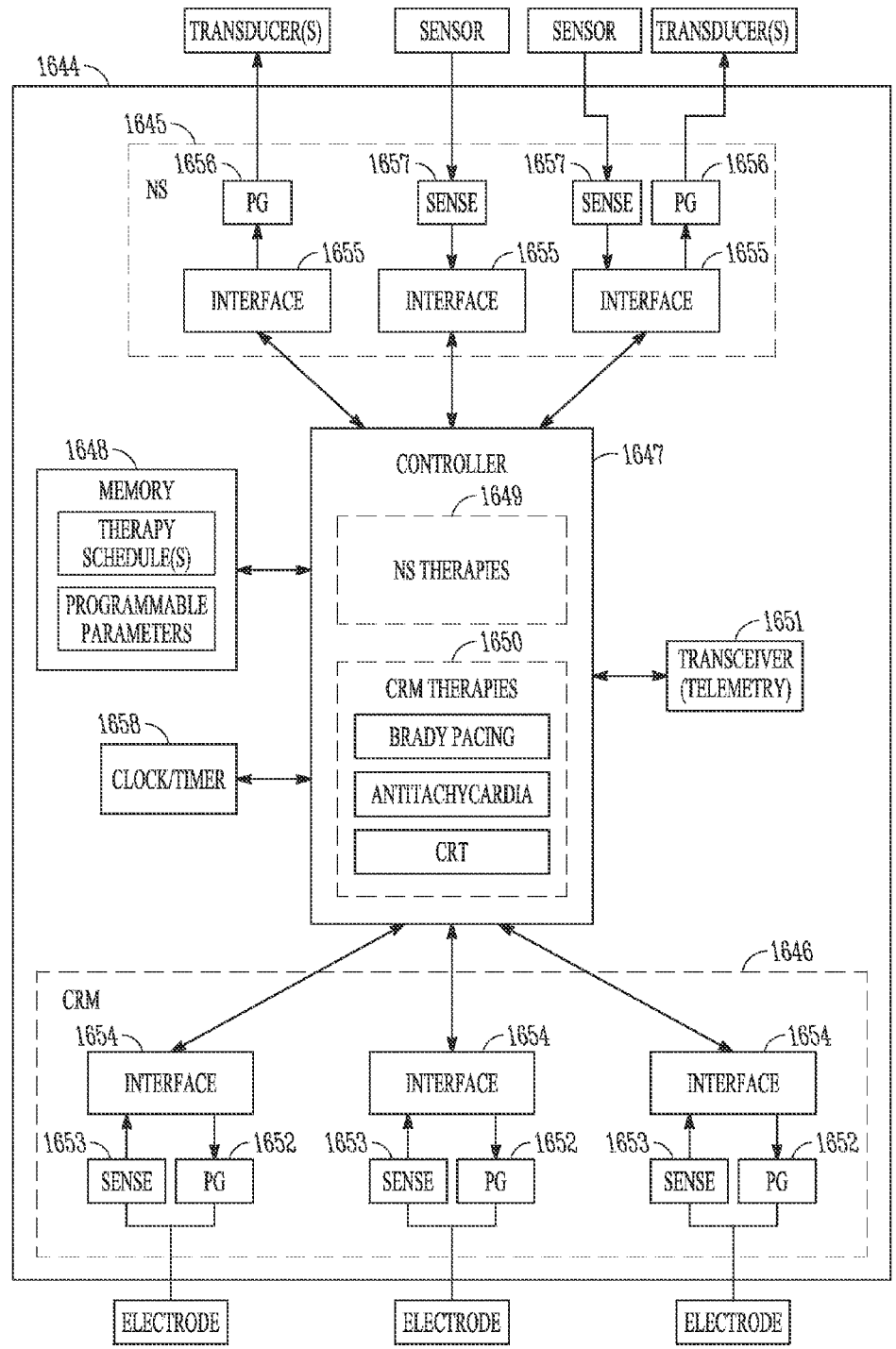
FIG. 16 illustrates an implantable medical device (IMD) having a neural stimulation (NS) component and a cardiac rhythm management (CRM) component according to various embodiments of the present subject matter.

FIG. 16 illustrates an implantable medical device (IMD) 1644 having a neural stimulation (NS) component 1645 and a cardiac rhythm management (CRM) component 1646 according to various embodiments of the present subject matter. The illustrated device includes a controller 1647 and memory 1648. According to various embodiments, the controller includes hardware, software, firmware or a combination thereof to perform the neural stimulation and CRM functions. For example, the programmed therapy applications discussed in this disclosure are capable of being stored as computer-readable instructions embodied in memory and executed by a processor. For example, therapy schedule(s) and programmable parameters can be stored in memory. According to various embodiments, the controller includes a processor to execute instructions embedded in memory to perform the neural stimulation and CRM functions. The illustrated neural stimulation therapy 1649 can include various neural stimulation therapies, such as a therapy for ventricular remodeling. Various embodiments include CRM therapies 1650, such as bradycardia pacing, anti-tachycardia therapies such as ATP, defibrillation and cardioversion, and cardiac resynchronization therapy (CRT). The illustrated device further includes a transceiver 1651 and associated circuitry for use to communicate with a programmer or another external or internal device. Various embodiments include a telemetry coil.

The CRM therapy section 1646 includes components, under the control of the controller, to stimulate a heart and/or sense cardiac signals using one or more electrodes. The illustrated CRM therapy section includes a pulse generator 1652 for use to provide an electrical signal through an electrode to stimulate a heart, and further includes sense circuitry 1653 to detect and process sensed cardiac signals. An interface 1654 is generally illustrated for use to communicate between the controller 1647 and the pulse generator 1652 and sense circuitry 1653. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 1645 includes components, under the control of the controller, to stimulate a neural stimulation target and/or sense parameters associated with nerve activity or surrogates of nerve activity such as blood pressure, heart rate and respiration. Three interfaces 1655 are illustrated for use to provide neural stimulation. However, the present subject matter is not limited to a particular number interfaces, or to any particular stimulating or sensing functions. Pulse generators 1656 are used to provide electrical pulses to transducer or transducers for use to stimulate a neural stimulation target. According to various embodiments, the pulse generator includes circuitry to set, and in some embodiments change, the amplitude of the stimulation pulse, the pulse width of the stimulation pulse, the frequency of the stimulation pulse, the burst frequency of the pulse, and the morphology of the pulse such as a square wave, sinusoidal wave, and waves with desired harmonic components. Sense circuits 1657 are used to detect and process signals from a sensor, such as a sensor of nerve activity, blood pressure, respiration, and the like. The interfaces 1655 are generally illustrated for use to communicate between the controller 1647 and the pulse generator 1656 and sense circuitry 1657. Each interface, for example, may be used to control a separate lead. Various embodiments of the NS therapy section only include a pulse generator to stimulate a neural target. The illustrated device further includes a clock/timer 1658, which can be used to deliver the programmed therapy according to a programmed stimulation protocol and/or schedule. The controller illustrated in FIG. 16 may include a response extractor, such as generally illustrated in FIG. 12. The controller illustrated in FIG. 16 also can control the therapy according to programmable therapy dose, duty cycle, and search parameters, as illustrated in FIG. 11.

Figure 17:
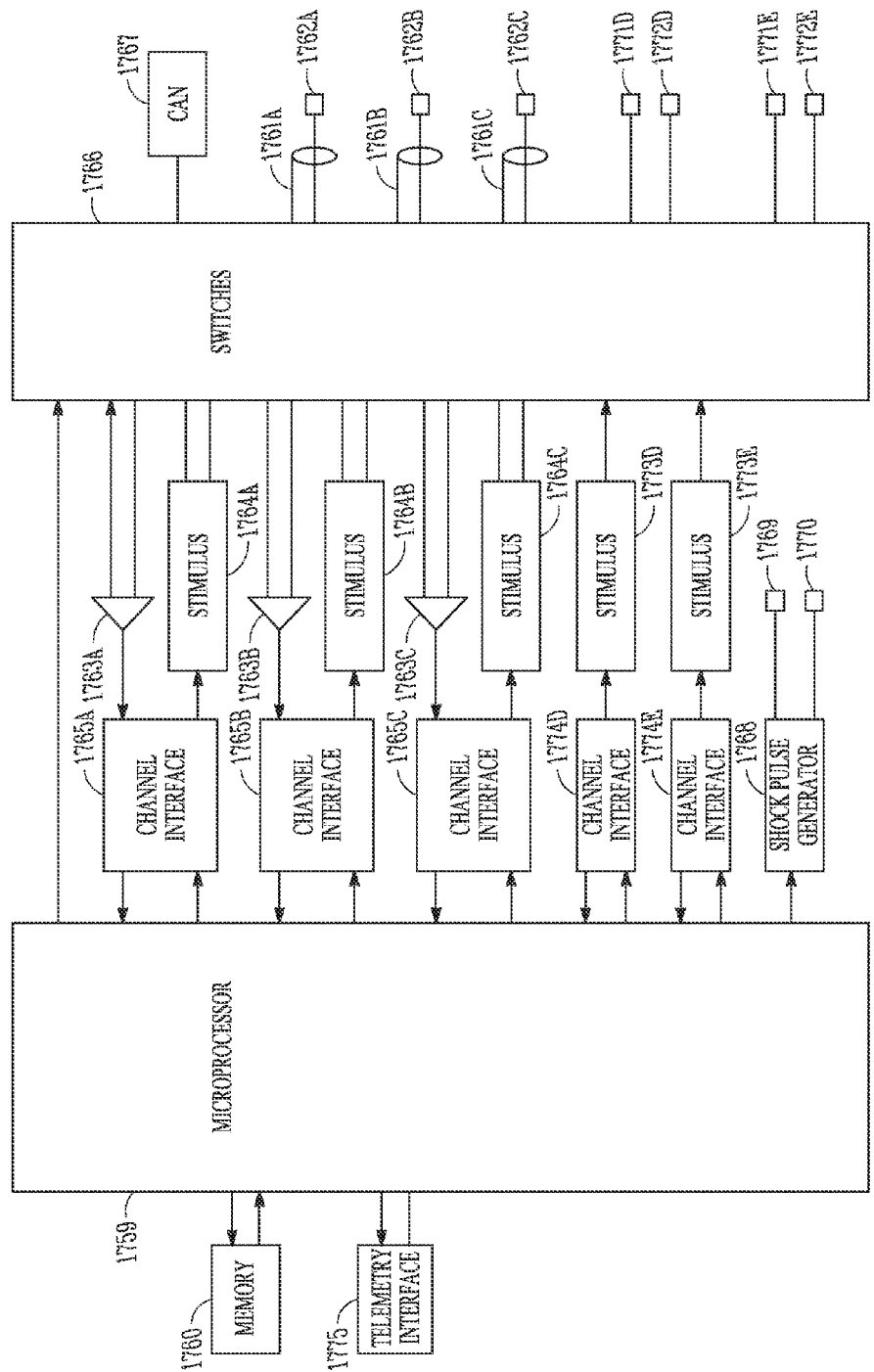
FIG. 17 shows a system diagram of an embodiment of a microprocessor-based implantable device, according to various embodiments.

FIG. 17 shows a system diagram of an embodiment of a microprocessor-based implantable device, according to various embodiments. The controller of the device is a microprocessor 1759 which communicates with a memory 1760 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 1761A-C and tip electrodes 1762A-C, sensing amplifiers 1763A-C, pulse generators 1764A-C, and channel interfaces 1765A-C. Each channel thus includes a pacing channel made up of the pulse generator connected to the electrode and a sensing channel made up of the sense amplifier connected to the electrode. The channel interfaces 1765A-C communicate bidirectionally with the microprocessor 1759, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 1766 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 1767 or an electrode on another lead serving as a ground electrode. Some embodiments provide a shock pulse generator 1768 interfaced to the controller for delivering a defibrillation shock via shock electrodes 1769 and 1770 to the atria or ventricles upon detection of a shockable tachyarrhythmia.

Neural stimulation channels, identified as channels D and E, are incorporated into the device for delivering parasympathetic and/or sympathetic excitation and/or parasympathetic and/or sympathetic inhibition, where one channel includes a bipolar lead with a first electrode 1771D and a second electrode 1772D, a pulse generator 1773D, and a channel interface 1774D, and the other channel includes a bipolar lead with a first electrode 1771E and a second electrode 1772E, a pulse generator 1773E, and a channel interface 1774E. Other embodiments may use unipolar leads in which case the neural stimulation pulses are referenced to the can or another electrode. Other embodiments may use tripolar or multipolar leads. In various embodiments, the pulse generator for each channel outputs a train of neural stimulation pulses which may be varied by the controller as to amplitude, frequency, duty-cycle, and the like. In some embodiments, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links.

The figure illustrates a telemetry interface 1775 connected to the microprocessor, which can be used to communicate with an external device. The illustrated microprocessor 1759 is capable of performing neural stimulation therapy routines and myocardial (CRM) stimulation routines. Examples of NS therapy routines include, but are not limited to, therapies to provide physical conditioning and therapies to treat ventricular remodeling, hypertension, sleep disordered breathing, blood pressure control such as to treat hypertension, cardiac rhythm management, myocardial infarction and ischemia, heart failure, epilepsy, depression, for pain, migraines, eating disorders and obesity, and movement disorders. The present subject matter is not limited to a particular neural stimulation therapy. Examples of myocardial therapy routines, but are not limited to, include bradycardia pacing therapies, anti-tachycardia shock therapies such as cardioversion or defibrillation therapies, anti-tachycardia pacing therapies (ATP), and cardiac resynchronization therapies (CRT).

Figure 18:
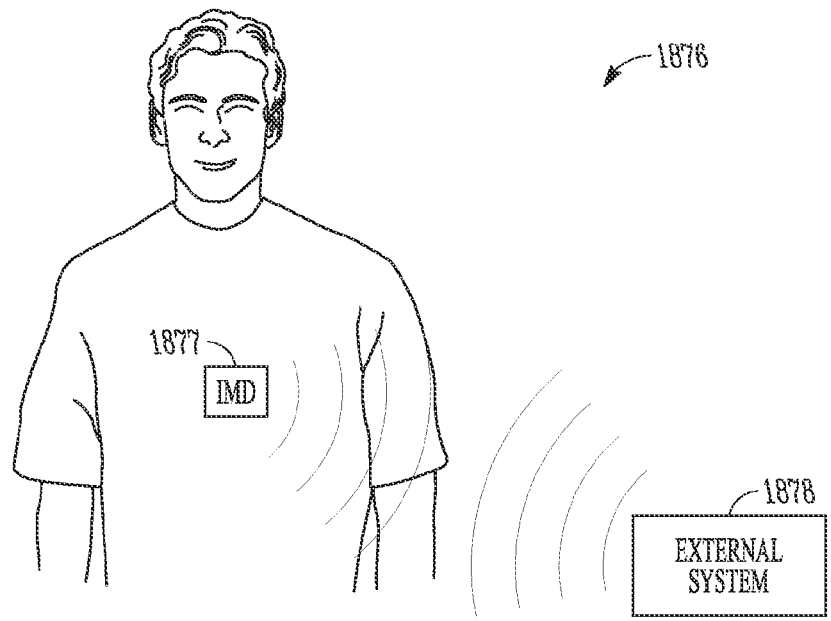
FIG. 18 illustrates a system including an implantable medical device (IMD) and an external system or device, according to various embodiments of the present subject matter.

FIG. 18 illustrates a system 1876 including an implantable medical device (IMD) 1877 and an external system or device 1878, according to various embodiments of the present subject matter. Various embodiments of the IMD include NS functions or include a combination of NS and CRM functions. The IMD may also deliver biological agents and pharmaceutical agents. The external system and the IMD are capable of wirelessly communicating data and instructions. In various embodiments, for example, the external system and IMD use telemetry coils to wirelessly communicate data and instructions. Thus, the programmer can be used to adjust the programmed therapy provided by the IMD, and the IMD can report device data (such as battery and lead resistance) and therapy data (such as sense and stimulation data) to the programmer using radio telemetry, for example. The external system allows a user such as a physician or other caregiver or a patient to control the operation of the IMD and obtain information acquired by the IMD. In one embodiment, the external system includes a programmer communicating with the IMD bi-directionally via a telemetry link. In another embodiment, the external system is a patient management system including an external device communicating with a remote device through a telecommunication network. The external device is within the vicinity of the IMD and communicates with the IMD bi-directionally via a telemetry link. The remote device allows the user to monitor and treat a patient from a distant location. The patient monitoring system is further discussed below. The telemetry link provides for data transmission from the implantable medical device to the external system. This includes, for example, transmitting real-time physiological data acquired by the IMD, extracting physiological data acquired by and stored in the IMD, extracting therapy history data stored in the implantable medical device, and extracting data indicating an operational status of the IMD (e.g., battery status and lead impedance). The telemetry link also provides for data transmission from the external system to the IMD. This includes, for example, programming the IMD to acquire physiological data, programming the IMD to perform at least one self-diagnostic test (such as for a device operational status), and programming the IMD to deliver at least one therapy.

Figure 19:
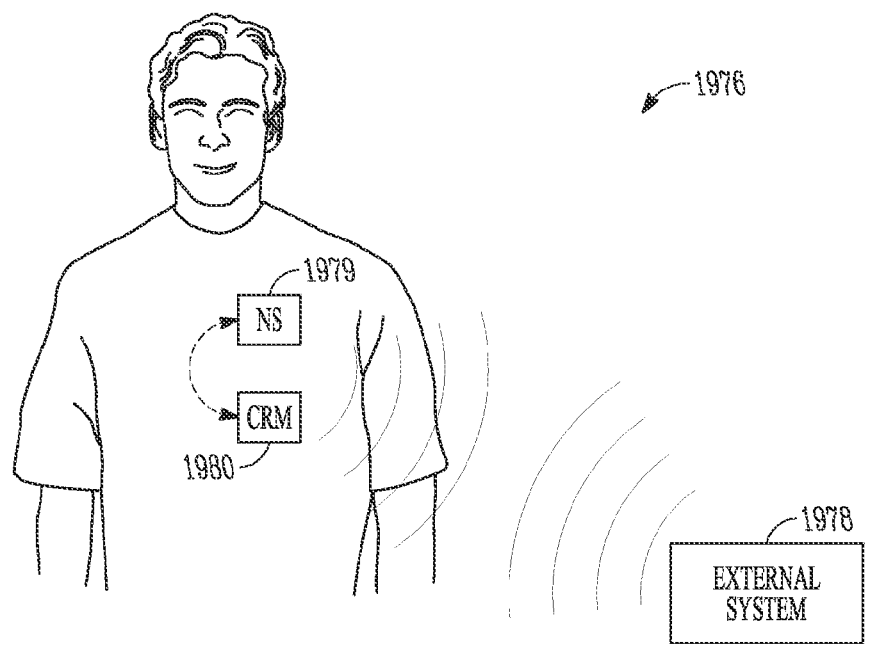
FIG. 19 illustrates a system including an external device, an implantable neural stimulator (NS) device and an implantable cardiac rhythm management (CRM) device, according to various embodiments of the present subject matter.

FIG. 19 illustrates a system 1976 including an external device 1978, an implantable neural stimulator (NS) device 1979 and an implantable cardiac rhythm management (CRM) device 1980, according to various embodiments of the present subject matter. Various aspects involve a method for communicating between an NS device and a CRM device or other cardiac stimulator. In various embodiments, this communication allows one of the devices 1967 or 1968 to deliver more appropriate therapy (i.e. more appropriate NS therapy or CRM therapy) based on data received from the other device. Additionally, the sensors from the CRM device may monitor HR, BP, or another parameter for the transient response to the neural stimulation. Some embodiments provide on-demand communications. In various embodiments, this communication allows each of the devices to deliver more appropriate therapy (i.e. more appropriate NS therapy and CRM therapy) based on data received from the other device. The illustrated NS device and the CRM device are capable of wirelessly communicating with each other, and the external system is capable of wirelessly communicating with at least one of the NS and the CRM devices. For example, various embodiments use telemetry coils to wirelessly communicate data and instructions to each other. In other embodiments, communication of data and/or energy is by ultrasonic means. Rather than providing wireless communication between the NS and CRM devices, various embodiments provide a communication cable or wire, such as an intravenously-fed lead, for use to communicate between the NS device and the CRM device. In some embodiments, the external system functions as a communication bridge between the NS and CRM devices.

FIGS. 20-23 illustrate system embodiments adapted to provide vagal stimulation, and are illustrated as bilateral systems that can stimulate both the left and right vagus nerve. Those of ordinary skill in the art will understand, upon reading and comprehending this disclosure, that systems can be designed to stimulate only the right vagus nerve, systems can be designed to stimulate only the left vagus nerve, and systems can be designed to bilaterally stimulate both the right and left vagus nerves. The systems can be designed to stimulate nerve traffic (providing a parasympathetic response when the vagus is stimulated), or to inhibit nerve traffic (providing a sympathetic response when the vagus is inhibited). Various embodiments deliver unidirectional stimulation or selective stimulation of some of the nerve fibers in the nerve.

Figure 20:
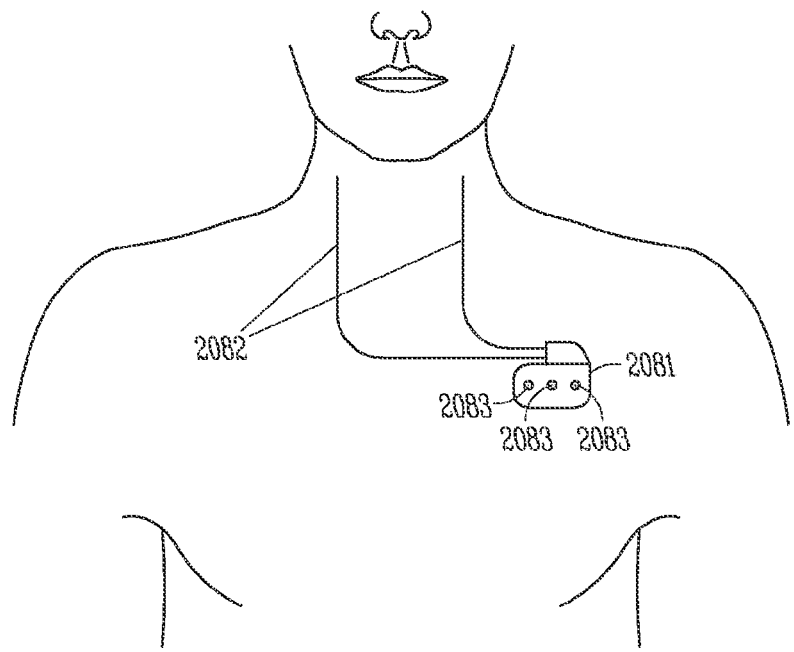
FIGS. 20-23 illustrate system embodiments adapted to provide vagal stimulation.

FIG. 20 illustrates a system embodiment in which an IMD 2081 is placed subcutaneously or submuscularly in a patient's chest with lead(s) 2082 positioned to stimulate a vagus nerve. According to various embodiments, neural stimulation lead(s) 2082 are subcutaneously tunneled to a neural target, and can have a nerve cuff electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. Other embodiments deliver neural stimulation to the neural target from within the trachea, the laryngeal branches of the internal jugular vein, and the subclavian vein. The neural targets can be stimulated using other energy waveforms, such as ultrasound and light energy waveforms. Other neural targets can be stimulated, such as cardiac nerves and cardiac fat pads. The illustrated system includes leadless ECG electrodes 2083 on the housing of the device. These ECG electrodes are capable of being used to detect heart rate, for example.

Figure 21:
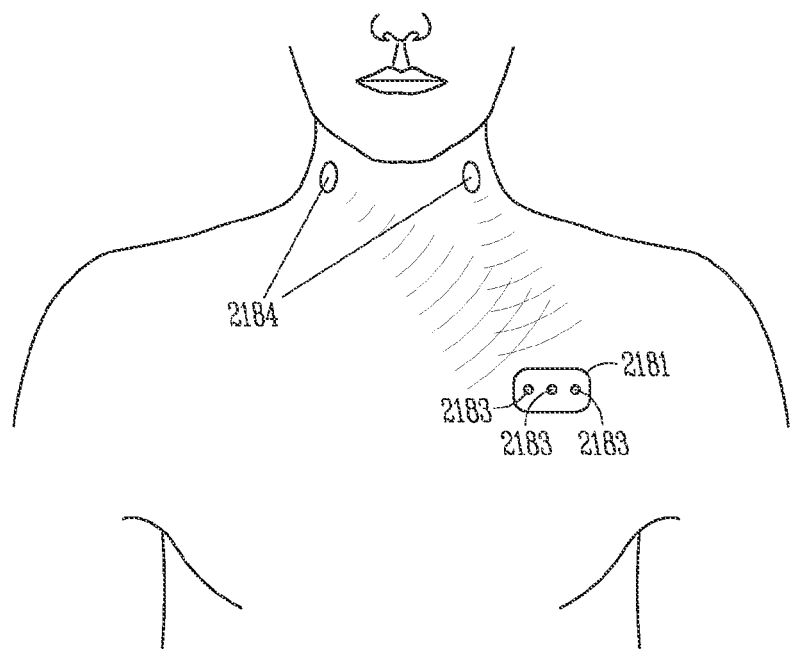

FIG. 21 illustrates a system embodiment that includes an implantable medical device (IMD) 2181 with satellite electrode(s) 2184 positioned to stimulate at least one neural target. The satellite electrode(s) are connected to the IMD, which functions as the planet for the satellites, via a wireless link. Stimulation and communication can be performed through the wireless link. Examples of wireless links include RF links and ultrasound links Examples of satellite electrodes include subcutaneous electrodes, nerve cuff electrodes and intravascular electrodes. Various embodiments include satellite neural stimulation transducers used to generate neural stimulation waveforms such as ultrasound and light waveforms. The illustrated system includes leadless ECG electrodes on the housing of the device. These ECG electrodes 2183 are capable of being used to detect heart rate, for example.

Figure 22:
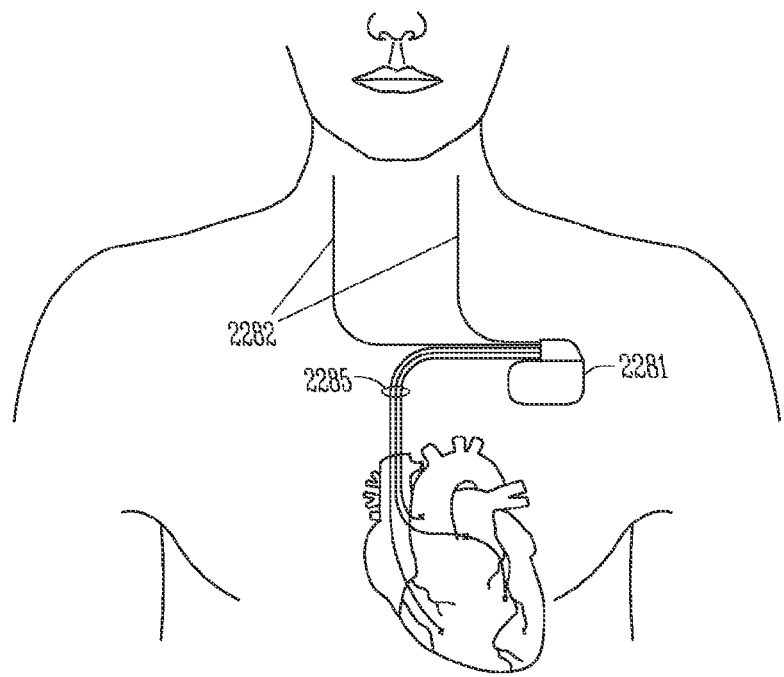

FIG. 22 illustrates an IMD 2281 placed subcutaneously or submuscularly in a patient's chest with lead(s) 2285 positioned to provide a CRM therapy to a heart, and with lead(s) 2282 positioned to stimulate and/or inhibit neural traffic at a neural target, such as a vagus nerve, according to various embodiments. According to various embodiments, neural stimulation lead(s) are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments target the vagus nerve using electrode(s) positioned within the internal jugular vein.

Figure 23:
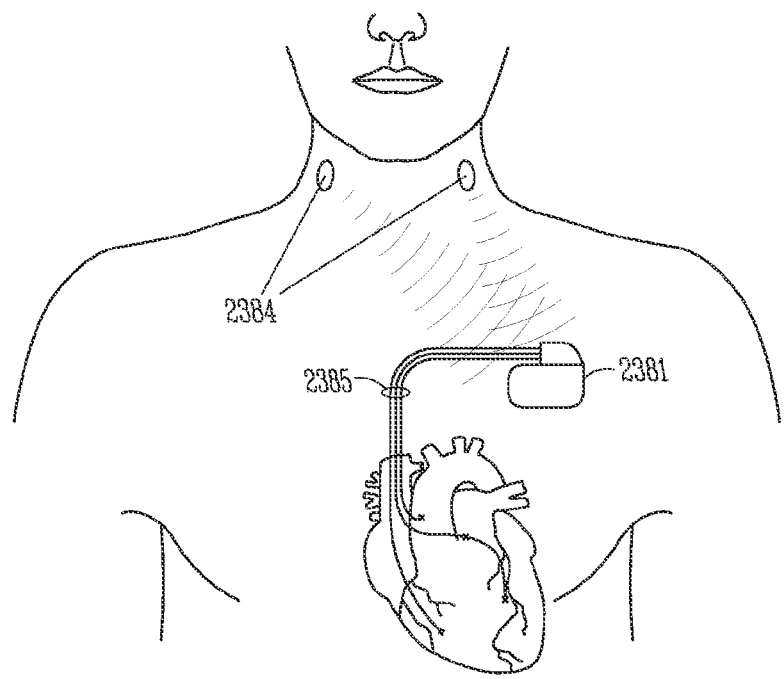

FIG. 23 illustrates an IMD 2381 with lead(s) 2385 positioned to provide a CRM therapy to a heart, and with satellite transducers 2384 positioned to stimulate/inhibit a neural target such as a vagus nerve, according to various embodiments. The satellite transducers are connected to the IMD, which functions as the planet for the satellites, via a wireless link. Stimulation and communication can be performed through the wireless link. Examples of wireless links include RF links and ultrasound links. Although not illustrated, some embodiments perform myocardial stimulation using wireless links. Examples of satellite transducers include subcutaneous electrodes, nerve cuff electrodes and intravascular electrodes.

Figure 24:
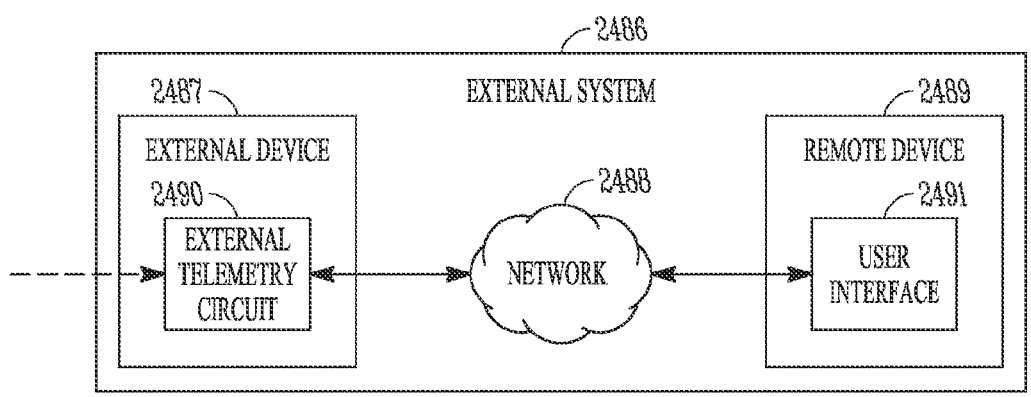
FIG. 24 is a block diagram illustrating an embodiment of an external system.

FIG. 24 is a block diagram illustrating an embodiment of an external system 2486. The external system includes a programmer, in some embodiments. In the illustrated embodiment, the external system includes a patient management system. As illustrated, the external system 2486 is a patient management system including an external device 2487, a telecommunication network 2488, and a remote device 2489. The external device 2487 is placed within the vicinity of an implantable medical device (IMD) and includes an external telemetry system 2490 to communicate with the IMD. The remote device(s) 2489 is in one or more remote locations and communicates with the external device 2487 through the network 2488, thus allowing a physician or other caregiver to monitor and treat a patient from a distant location and/or allowing access to various treatment resources from the one or more remote locations. The illustrated remote device 2489 includes a user interface 2491. According to various embodiments, the external device 2487 includes a neural stimulator, a programmer or other device such as a computer, a personal data assistant or phone. The external device 2487, in various embodiments, includes two devices adapted to communicate with each other over an appropriate communication channel. The external device can be used by the patient or physician to provide side effect feedback indicative of patient discomfort, for example.

Therapies

The present subject matter relates to systems, devices and methods for providing neural stimulation, such as vagus nerve stimulation, and further relates to delivering neural stimulation therapy (NST) or vagal nerve modulation (VNM) with a stimulation signal at a location determined to provide a desired transient evoked response to the stimulus. The present subject matter can be applied to neurostimulation therapies used to treat cardiovascular diseases, such as heart failure, tachyarrhythmia, hypertension, and atherosclerosis. Various embodiments provide a stand-alone device, either externally or internally, to provide neural stimulation therapy. The present subject matter can be implemented in cardiac applications for neural stimulation or in non-cardiac applications for neural stimulation where a diverse nerve (such as the vagus nerve) is stimulated. For example, the present subject matter may deliver anti-remodeling therapy through neural stimulation as part of a post-MI or heart failure therapy. Various embodiments provide systems or devices that integrate neural stimulation with one or more other therapies, such as bradycardia pacing, anti-tachycardia therapy, remodeling therapy, and the like.

Neural Stimulation Therapies

Examples of neural stimulation therapies include neural stimulation therapies for respiratory problems such a sleep disordered breathing, for blood pressure control such as to treat hypertension, for cardiac rhythm management, for myocardial infarction and ischemia, for heart failure, for epilepsy, for depression, for pain, for migraines, for eating disorders and obesity, for movement disorders, for cardiovascular disease, for metabolic disease, for inflammatory disease and for atherosclerosis. Many proposed neural stimulation therapies include stimulation of an autonomic neural target such as the vagus nerve. This listing of other neural stimulation therapies is not intended to be an exhaustive listing. Neural stimulation can be provided using electrical, acoustic, ultrasound, light, and magnetic therapies. Electrical neural stimulation can be delivered using any of a nerve cuff, intravascularly-fed lead, or transcutaneous electrodes.

Various embodiments of the present subject matter deliver vagal nerve modulation (VNM) to treat a variety of cardiovascular disorders, including heart failure, post-MI remodeling, and hypertension. These conditions are briefly described below.

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease.

Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Sympathetic activity is pathologically elevated in HF and detrimental over the long term. This situation is characterized by excessive release of norepinephrine (NE), so much so that myocardial adrenergic receptors are down-regulated as the heart tries to protect itself from the excessive myocardial infarction (MI). A drug strategy augments this protective response by blocking the remaining myocardial adrenergic receptors. However, parasympathetic activity is actively depressed in heart failure (HF), and this depressed parasympathetic activity has largely been ignored for HF treatment. In particular, acetylcholine (ACh) release in the heart is presynaptically inhibited by angiotensin II, which is markedly elevated in HF. In response to this lack of ACh, the myocardial muscarinic receptors are markedly upregulated to try to increase the effects of ACh. Also parasympathetic reflexes, such as the baroreceptor reflex, are inhibited by the increased sympathetic activity.

The vagus nerve can be stimulated in the cervical region with implanted nerve cuff electrodes attached via a lead to an implanted pulse generator in the chest. Based on preclinical studies, this VNM has been found to prevent left ventricular dilatation and improve pump function (left ejection fraction) when administered for three months following induction of HF by microembolism in dogs. Thus, VNM may be a treatment for HF disease and symptoms. It is believed that VNM may counterbalance the depressed parasympathetic levels that occur during HF. The VNM that was successful in the preclinical studies at treating the HF was administered with periods of approximately 10 second stimulation bursts once every minute. The stimulation during the burst was a series of electrical pulses around 1 mA and around 20 Hz. In other words, the stimulation protocol includes intermittent bursts (e.g. 10 second bursts) of stimulation. Each burst includes a plurality of pulses delivered at a pulse frequency (e.g. 20 Hz) during the burst (e.g. throughout the 10 second burst). The burst of pulses also may be delivered at a burst frequency (e.g. 1 burst/60 seconds) if the burst stimulation period of one minute is used. VNM can modulate parasympathetic cardiovascular activity, as indicated by the measured effects of this stimulation on heart rate (HR) and blood pressure (BP).

Figure 25:
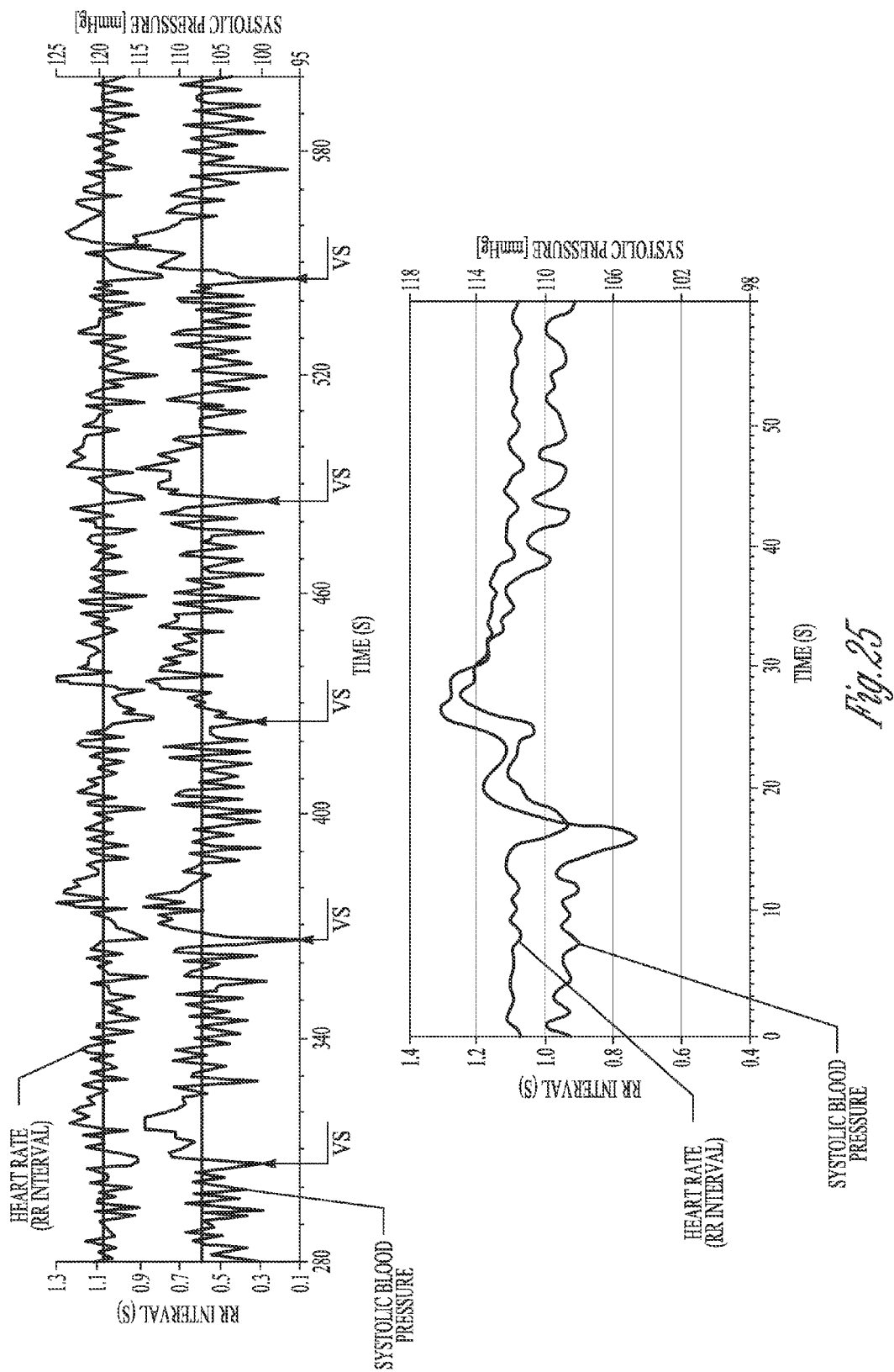
FIGS. 25-27 illustrate preclinical study results.
Figure 26:
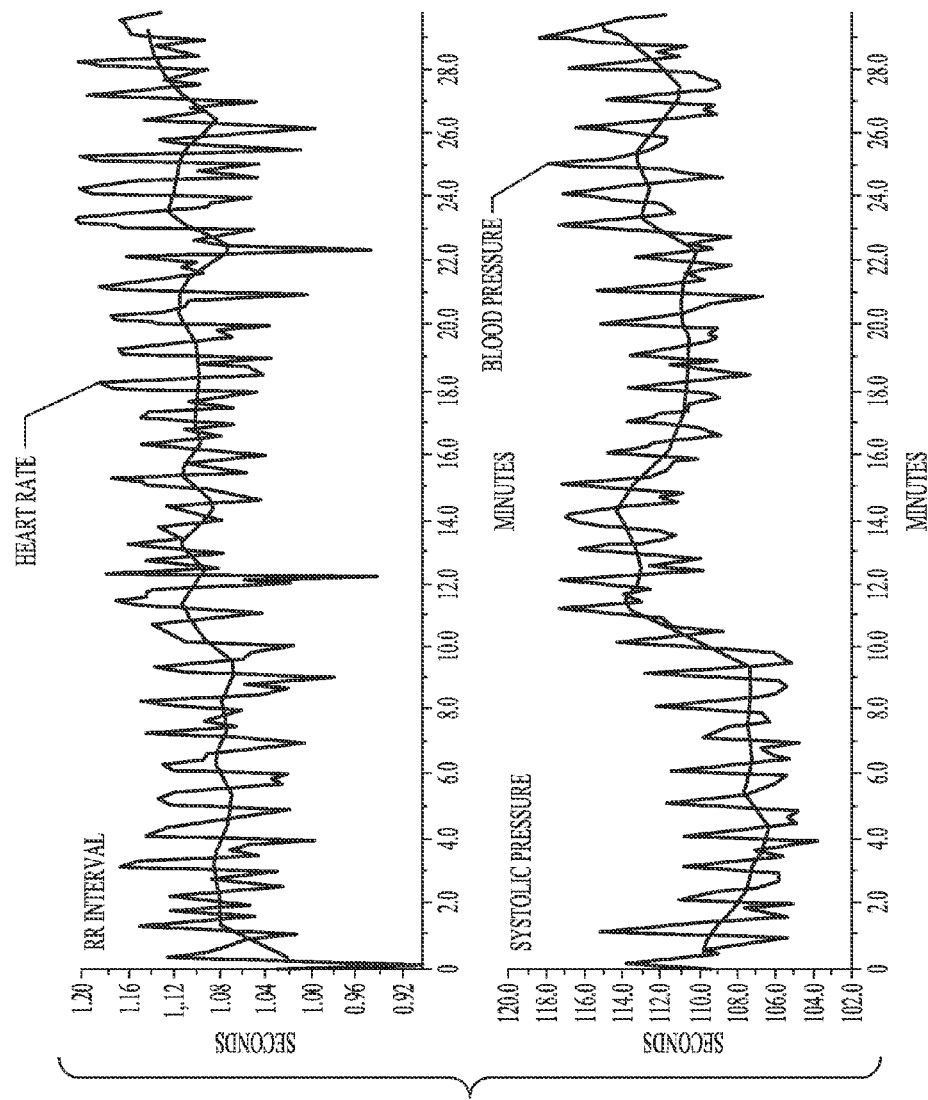
Figure 27:
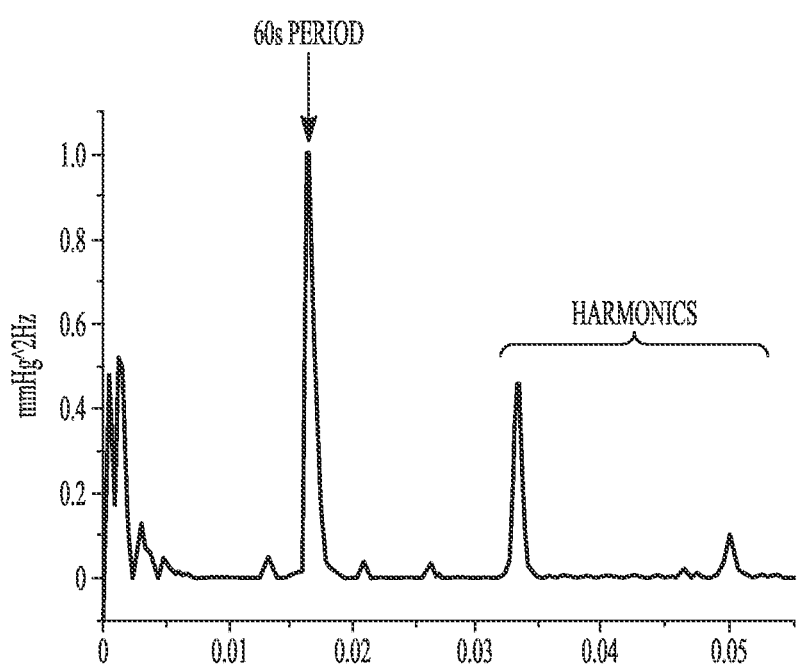

FIGS. 25-27 illustrate preclinical study results. In FIG. 25, HR (RR interval) and BP (systolic pressure) recordings are shown from a sheep stimulated with the above VNM protocol. The example shows that intermittent VNM can elicit periodic oscillations of HR and BP without changing mean HR and BP. The upper panel shows HR and BP responses to a series of five 10 second bursts of vagal stimulation (VS) separated by 50 seconds of no stimulation. The lower panel shows the signal averaged HR and BP responses for the one minute intermittent stimulation period. The direct effect of the stimulation decreases the BP, which in turn elicits a reflex response that transiently increases the HR (decreases the R-to-R heart beat interval as shown on the graph). As the direct stimulation ends, BP rebounds and increases above baseline due to a reflex response to the directly decreased BP. These HR and BP oscillations are allowed to wash out before the next stimulation such that there is not a significant change in the average heart rate or blood pressure over the intermittent stimulation period (e.g. 10 second stimulation bursts separated by 50 seconds of no stimulation). These HR and BP oscillations are the result of directly and reflexively modulating ANS activity. FIG. 26 illustrates changes in the HR (RR interval) and systolic BP over a 30 minute period while stimulating the vagus with a 10 second burst every 60 seconds. Every minute, the RR interval oscillates +7 bpm around a randomly fluctuating mean, and correspondingly, systolic BP oscillates about +7 mmHg around a randomly fluctuating mean. The fluctuations in HR and BP means are uncorrelated with the intermittent neural stimulation, and rather reflect natural influences on HR and BP that have a different time scale than the stimulation period. FIG. 27 shows the Fast Fourier Transform power spectrum of the BP signal, which indicates that the signal is dominated by a once-per-minute (60 second period) modulation corresponding to the VNM duty cycle of a 10 second burst every minute.

When a neural stimulation therapy is delivered with a step up to the therapeutic intensity at the beginning of a duty cycle, and a step down at the end of the duty cycle, transients have been observed in the neurological system. For example, abrupt changes in parasympathetic neural stimulation intensity can result in sympathetic tone rebound. For example, upon conclusion of a stimulation pulse train that elicits a parasympathetic response, there is sympathetic tone rebound that is reflected in increased HR and increased BP. Possible mechanisms involved with the observed rebound may include the activation of the baroreflex and/or chemoreflex.

In the preclinical study illustrated in FIGS. 25-27, it is believed that the VNM device and protocol are directly decreasing BP for the 10 seconds it is on (bursting). This triggers baroreceptor signals indicating that BP should be increased, which elicits a reflex sympathetic activation that increases HR. After the direct NS response ends, the sympathetic activation also increases BP. The baroreceptors respond again, now to the increased BP, and elicit a reflex parasympathetic activation that decreases HR and BP back toward baseline. The reflex-mediated oscillations of HR and BP are allowed to wash out before the next stimulation. Various embodiments of the present subject matter intermittently or periodically stimulate ANS cardiac actions both directly and reflexively and without changing or significantly altering mean HR or BP. Various embodiments can either directly stimulate parasympathetic actions or sympathetic actions or both kinds of actions.

Some embodiments deliver direct and reflex (e.g., baroreceptor reflex) stimulation of the cardiovascular parasympathetic neural pathways with one vagus nerve stimulation site/lead. One embodiment in this case selectively stimulates the vagus nerve cardiac efferent (motoneuron) axons that have a direct effect on HR and/or BP. In some embodiments, the duration and magnitude of a stimulation burst is timed to activate baroreceptor reflexes that have an equal magnitude but opposite effect on HR and BP. Another embodiment selectively stimulates the vagus nerve afferent axons that directly activate central nervous system networks controlling BP, causing BP to oscillate during and after the VNM stimulation burst and indirectly causing HR to oscillate reflexively in response to the BP oscillations.

A therapy embodiment involves preventing and/or treating ventricular remodeling. Activity of the autonomic nervous system is at least partly responsible for the ventricular remodeling which occurs as a consequence of an MI or due to heart failure. It has been demonstrated that remodeling can be affected by pharmacological intervention with the use of, for example, ACE inhibitors and beta-blockers. Pharmacological treatment carries with it the risk of side effects, however, and it is also difficult to modulate the effects of drugs in a precise manner. Embodiments of the present subject matter employ electrostimulatory means to modulate autonomic activity, referred to as anti-remodeling therapy or ART. When delivered in conjunction with ventricular resynchronization pacing, also referred to as remodeling control therapy (RCT), such modulation of autonomic activity may act synergistically to reverse or prevent cardiac remodeling.

One neural stimulation therapy embodiment involves treating hypertension by stimulating the baroreflex for sustained periods of time sufficient to reduce hypertension. The baroreflex is a reflex that can be triggered by stimulation of a baroreceptor or an afferent nerve trunk. Baroreflex neural targets include any sensor of pressure changes (e.g. sensory nerve endings that function as a baroreceptor) that is sensitive to stretching of the wall resulting from increased pressure from within, and that functions as the receptor of the central reflex mechanism that tends to reduce that pressure. Baroreflex neural targets also include neural pathways extending from the baroreceptors. Baroreflex neural targets can be found in the wall of the auricles of the heart, cardiac fat pads, vena cava, aortic arch and carotid sinus. Examples of afferent nerve trunks that can serve as baroreflex neural targets include the vagus, aortic and carotid nerves. Stimulating baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of the arterial wall. Chemoreceptors, which are sensory nerve cells that respond to chemical stimuli, may be stimulated to stimulate a desired autonomic reflex response. Some aspects of the present subject matter locally stimulate specific nerve endings in arterial walls rather than stimulate afferent nerve trunks in an effort to stimulate a desired response (e.g. reduced hypertension) while reducing the undesired effects of indiscriminate stimulation of the nervous system. For example, some embodiments stimulate baroreceptor sites in the pulmonary artery. Some embodiments of the present subject matter involve stimulating either baroreceptor sites or nerve endings in the aorta, the chambers of the heart, the fat pads of the heart, and some embodiments of the present subject matter involve stimulating an afferent nerve trunk, such as the vagus, carotid and aortic nerves. Some embodiments stimulate afferent or efferent nerve trunks using a cuff electrode, and some embodiments stimulate afferent nerve trunks using an intravascular lead positioned in a blood vessel proximate to the nerve, such that the electrical stimulation passes through the vessel wall to stimulate the afferent nerve trunk.

Neural stimulation (e.g. sympathetic nerve stimulation and/or parasympathetic nerve inhibition) can mimic the effects of physical conditioning. It is generally accepted that physical activity and fitness improve health and reduce mortality. Studies have indicated that aerobic training improves cardiac autonomic regulation, reduces heart rate and is associated with increased cardiac vagal outflow. A baseline measurement of higher parasympathetic activity is associated with improved aerobic fitness. Exercise training intermittently stresses the system and increases the sympathetic activity during the stress. However, when an exercise session ends and the stress is removed, the body rebounds in a manner that increases baseline parasympathetic activity and reduces baseline sympathetic activity. Physical conditioning can be considered to be a repetitive, high-level exercise that occurs intermittently over time. Physical conditioning therapy can be applied as therapy for heart failure. Examples of other physical conditioning therapies include therapies for patients who are unable to exercise. For example, physical conditioning using sympathetic stimulation/parasympathetic inhibition for a bed-bound, post-surgical patient in a hospital may enable the patient to maintain strength and endurance until such time that the patient is able to exercise again. By way of another example, a morbidly obese patient may be unable to exercise, but may still benefit from the physical conditioning therapy. Furthermore, patients with injuries such as joint injuries that prevent them from performing their normal physical activities may benefit from the physical conditioning therapy.

Embodiments described herein can be used to treat diseases associated with depressed parasympathetic levels and activity in patients intolerant of tonic decreases in heart rate or blood pressure. Examples of such diseases associated with depressed parasympathetic levels include HF, MI, tachyarrhythmia, hypertension, atherosclerosis. Because mean HR and BP are not significantly altered using the stimulation protocol that drives oscillations in HR and BP, the device provides beneficial results of increased parasympathetic tone while avoiding potential side-effects of previous devices and methods for vagal stimulation, which can cause bradycardia and hypotension. For example, an embodiment increases heart rate variability (HRV) (or other indicators of autonomic tone) without changing mean HR. This may be beneficial in patients with reduced HRV, such as advanced HF patients, who are also on medications that already lower their HR.

An embodiment includes an implantable vagus nerve stimulator for treatment of cardiovascular diseases associated with depressed parasympathetic levels, such as HF. An embodiment intermittently or periodically (e.g. once per minute) increases parasympathetic levels and actions by direct parasympathetic nerve stimulation and reflex activation of evoked parasympathetic responses in a way that modulates HR and BP during the periodic stimulation without changing or significantly altering the mean HR or BP. That is, the device delivers stimulation to efferent pathways to provide the direct response, and also delivers stimulation to afferent pathways to induce a reflex response. Some devices are capable of independently controlling the efferent and afferent stimulation. This provides a dual therapy (direct and reflex parasympathetic activation) that is safe for patients at risk of bradycardia or hypotension from vagus nerve stimulation.

An embodiment includes an implantable vagus nerve stimulator adapted to increase parasympathetic levels and activity with intermittent or periodic (e.g., on the order of 10 seconds once per minute) modulatory stimulation that is associated with periodic HR and BP oscillations without significantly altering mean HR or mean BP over an approximately one minute time scale.

Myocardial Stimulation Therapies

Various neural stimulation therapies can be integrated with various myocardial stimulation therapies. The integration of therapies may have a synergistic effect. Therapies can be synchronized with each other, and sensed data can be shared between the therapies. A myocardial stimulation therapy provides a cardiac therapy using electrical stimulation of the myocardium. Some examples of myocardial stimulation therapies are provided below.

A pacemaker is a device which paces the heart with timed pacing pulses, most commonly for the treatment of bradycardia where the ventricular rate is too slow. If functioning properly, the pacemaker makes up for the heart's inability to pace itself at an appropriate rhythm in order to meet metabolic demand by enforcing a minimum heart rate. Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrioventricular delay interval with respect to the detection of an intrinsic atrial contraction or delivery of an atrial pace.

CRT can be beneficial in reducing the deleterious ventricular remodeling which can occur in post-MI and heart failure patients. Presumably, this occurs as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle near the infarcted region in a manner which may cause a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of CRM devices known as an implantable cardioverter defibrillator (ICD) provides this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected.

Some embodiments provide a NS device configured to communicate, either wired or wireless, with other implantable devices that have sensors for measuring short and long term physiological responses of the neurostimulation. These responses can be used to measure the transient response and to measure clinical responses.

One of ordinary skill in the art will understand that, the modules and other circuitry shown and described herein can be implemented using software, hardware, firmware and combinations thereof.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method comprising:
    using a neural stimulator system to deliver neural stimulation therapy, wherein
        the neural stimulation therapy includes a plurality of neural stimulation bursts,
        each neural stimulation burst includes a plurality of neural stimulation pulses, and
        successive neural stimulation bursts are separated by a time without neural stimulation pulses;
    evaluating, using the neural stimulator system, an evoked response to the neural stimulation bursts of the neural stimulation therapy, wherein evaluating the evoked response includes:
        sensing the evoked response to the neural stimulation bursts, wherein sensing the evoked response includes sensing at least one physiological parameter affected by the neural stimulation bursts; and
        performing a statistical analysis of the evoked response to the plurality of neural stimulation bursts to determine if the neural stimulation bursts provide a desired evoked response for the neural stimulation therapy; and
    performing an action using the neural stimulation system including:
        changing neural stimulation parameters for the neural stimulation therapy if the evoked response does not provide the desired evoked response, or
        recording results of the statistical analysis for access by a clinician.

2. The method of claim 1, wherein the action includes changing the neural stimulation parameters and further includes using the statistical analysis of the evoked response to change the neural stimulation parameters.

3. The method of claim 1, wherein the action includes using the neural stimulation system to automatically record results of the comparison in a memory of the implantable neural stimulator for access by a clinician.

4. The method of claim 3, further comprising sampling the evoked response based on timing of neural stimulation events to provide event samples, wherein performing the statistical analysis of the evoked response includes performing a statistical analysis of the event samples.

5. The method of claim 1, wherein sensing at least one physiological parameter includes sensing heart rate.

6. The method of claim 1, wherein sensing at least one physiological parameter includes sensing blood pressure.

7. The method of claim 1, wherein evaluating the evoked response includes comparing a pattern of the evoked response to a template.

8. The method of claim 1, wherein:
sensing at least one physiological parameter includes providing a time-series of parameter data points, and sampling the data points to provide a pre-stimulation data sample and a post-stimulation data sample; and
performing the statistical analysis includes performing an autocorrelation of the pre-stimulation data sample and the post-stimulation data sample.

9. The method of claim 1, wherein:
sensing at least one physiological parameter includes providing a time-series of parameter data points, and sampling the data points to provide a series of samples of a fixed duration; and
performing the statistical analysis includes performing a cross-correlation of the series of samples for the plurality of neural stimulation bursts.

10. The method of claim 1, wherein:
sensing at least one physiological parameter includes providing a time-series of parameter data points and sampling the data points to provide pre-stimulation data samples and to post-stimulation data samples; and
performing the statistical analysis includes performing a statistical analysis using the pre-stimulation data samples and post-stimulation data samples.

11. The method of claim 1, wherein sensing at least one physiological parameter includes providing a time-series of parameter data points, and evaluating the evoked response includes performing a Fourier decomposition of the time-series of parameter data points.

12. The method of claim 1, wherein the neural stimulation therapy includes a burst duration on the order of 10 seconds for the burst of neural stimulation pulses, a pulse frequency on the order of 20 Hz, and a burst period on the order of one minute.

13. The method of claim 1, wherein using the implantable neural stimulator to deliver the neural stimulation therapy to the autonomic neural target includes stimulating a vagus nerve.

14. The method of claim 13, wherein stimulating the vagus nerve includes selecting to stimulate at a first location or a different second location along the vagus nerve to control a distance that action potentials travel through the vagus nerve.

15. A system, comprising:
a neural stimulator configured to generate stimulation energy to stimulate the autonomic neural target;
a memory with a programmed neural stimulation therapy stored therein, wherein the therapy includes a plurality of programmable neural stimulation parameters for use in controlling a dose of the neural stimulation therapy, wherein the neural stimulation therapy includes a plurality of neural stimulation bursts, each burst includes a plurality of neural stimulation pulses, and successive bursts are separated by a time without neural stimulation pulses;
a controller configured to communicate with the memory and the neural stimulator to control the neural stimulation therapy using the programmable parameters;
a sensor adapted to sense at least one physiological parameter affected by the neural stimulation bursts and indicative of an evoked response to the neural stimulation therapy; and
a response extractor configured to receive a time series of parameter data from the sensor and to extract evoked response data from the time series of parameter data and configured to perform a statistical analysis of the evoked response data to the plurality of neural stimulation bursts to determine if the neural stimulation bursts provide a desired evoked response for the neural stimulation therapy,
wherein the device is configured to perform an action including:
changing neural stimulation parameters for the neural stimulation therapy if the evoked response does not provide the desired evoked response; or
recording results of the statistical analysis for access by a clinician.

16. The device of claim 15, wherein the controller is configured to use the statistical analysis of the evoked response data to adjust the neural stimulation parameters.

17. The device of claim 15, wherein the sensor is configured to sense at least one physiological parameter indicative of an initial response to the neural stimulation, the response extractor is configured to extract initial response data, and the controller is configured to use the extracted initial response data to adjust the neural stimulation parameters.

18. The system of claim 15, wherein the sensor includes a heart rate sensor, and the response extractor is configured to extract evoked heart rate response data and perform a statistical analysis of the evoked heart rate response data.

19. The system of claim 15, wherein the sensor includes a blood pressure sensor, and the response extractor is configured to extract evoked blood pressure response data and perform a statistical analysis of the evoked blood pressure response data.

20. The system of claim 15, wherein the response extractor is configured to provide a pre-stimulation data samples and post-stimulation data samples, and is further configured to perform a statistical analysis using the pre-stimulation data samples and the post-stimulation data samples.

* * * * *